United States Patent
Kurosawa et al.

(10) Patent No.: US 7,018,823 B2
(45) Date of Patent: Mar. 28, 2006

(54) FRUCTOSYL PEPTIDE OXIDASE

(75) Inventors: Keiko Kurosawa, Chiba (JP); Kozo Hirokawa, Chiba (JP); Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 147 days.

(21) Appl. No.: 10/232,655

(22) Filed: Sep. 3, 2002

(65) Prior Publication Data

US 2003/0157593 A1   Aug. 21, 2003

(30) Foreign Application Priority Data

| Sep. 4, 2001 | (JP) | 2001-266665 |
| Dec. 12, 2001 | (JP) | 2001-378151 |
| Aug. 6, 2002 | (JP) | 2002-228727 |

(51) Int. Cl.
 C12N 9/02    (2006.01)
 C12N 15/00   (2006.01)
 C12N 1/20    (2006.01)
 C12Q 1/26    (2006.01)
 C07H 21/04   (2006.01)

(52) U.S. Cl. ............. 435/189; 435/4; 435/6; 435/440; 435/252.3; 435/320.1; 435/69.1; 435/71.1; 435/25; 536/23.2; 536/23.7

(58) Field of Classification Search ........ 435/189, 435/440, 4, 6, 252.3, 320.1, 25, 69.1, 71.1; 536/23.2, 23.7
See application file for complete search history.

(56) References Cited

U.S. PATENT DOCUMENTS

| 5,789,221 A | * | 8/1998 | Kato et al. ........... 435/190 |
| 5,972,671 A | * | 10/1999 | Kato et al. ........... 435/191 |
| 6,033,867 A | * | 3/2000 | Kato et al. ........... 435/25 |

FOREIGN PATENT DOCUMENTS

| EP | 0 709 457 | 5/1996 |
| WO | WO 97/21818 | 6/1997 |
| WO | WO 01/25475 | 4/2001 |

OTHER PUBLICATIONS

Sequence Alignment—Yoshida et al. oxidase.*

(Continued)

*Primary Examiner*—Manjunath Rao
*Assistant Examiner*—Yong Pak
(74) *Attorney, Agent, or Firm*—Oblon, Spivak, McClelland, Maier & Neustadt, P.C.

(57) ABSTRACT

The present invention has an object of providing a novel fructosyl peptide oxidase having superior physicochemical properties such as stability that is useful as an enzyme for clinical diagnosis, and an object of providing a method for producing the fructosyl peptide oxidase.

A novel fructosyl peptide oxidase having physicochemical properties useful as an enzyme for clinical diagnosis, and a method for producing a novel fructosyl peptide oxidase are provided herein, the method comprising: culturing a microorganism capable of producing the oxidase in a medium; and collecting the oxidase from the culture. Furthermore, a fructosyl peptide oxidase gene coding for a novel fructosyl peptide oxidase, recombinant DNA wherein the gene is inserted into vector DNA, and a method for producing a novel fructosyl peptide oxidase are provided herein, the method comprising: culturing, in a medium, a transformant or a transductant including the gene; and collecting the novel fructosyl peptide oxidase from the culture.

18 Claims, 12 Drawing Sheets

OTHER PUBLICATIONS

N. Yoshida, et al., European Journal of Biochemistry, vol. 242, No. 3, pp. 499-505, XP-002089646, "Primary Structures of Fungal Fructosyl Amino Acid Oxidases and Their Application to the Measurement of Glycated Proteins", Dec. 15, 1996.

N. Yoshida, et al., Applied and Environmental Microbiology, vol. 61, No. 12, pp. 4487-4489, XP-000561863, "Distribution and Properties of Fructosyl Amino Acid Oxidase in Fungi", Dec. 1, 1995.

* cited by examiner

- ■ Acetic Acid
- ● MES
- ▲ Tris
- ♦ Potassium Phosphate
- □ Glycine

- ■ Acetic Acid
- ● MES
- ▲ Tris
- ♦ Potassium Phosphate
- □ Glycine

SEQUENCE LISTING

<160> NUMBER OF SEQ ID NOS: 24

<210> SEQ ID NO 1
<211> LENGTH: 437
<212> TYPE: PRT
<213> ORGANISM: Coniochaeta sp.

<400> SEQUENCE: 1

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110
```

```
Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asn
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys His Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys His Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atacgactgc gcaacaaggt ggacctgcaa atgagtctag aggctagaca gatgtggaag     240
```

```
gaggatgagt tattccagcc cttctttcac aataccggca gaatggactg cgaacacacg    300
cctgagggta tcgaggacct gaaaaagcag taccaggcac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtgg tgtaaagttc    540 ggattcggcg gcgctggatc cttcaagcaa ccccttttcg acgatgaagg cacaacttgc    600
attggcgttg agacggcaga tggtaccaaa tattacgctg acaaggtggt cttagcagct    660
ggcgcatgga gcccaaccct ggtggacctg aagatcaat gttgctcgaa ggcttgggtg    720
tatgctcata ttcagttgac gcctgaagag gccgctgagt ataagggtgt cccagttgtg    780
tataatggcg aatttggctt cttctttgag cctaatgagt ttggtgtaat aaaggtgtgc    840
gacgaattcc caggattctc gcgcttcaag gaacatcaac cctatggcgc cccatctccg    900
aaacacatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa acatgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa          1314

<210> SEQ ID NO 3
<211> LENGTH: 437
<212> TYPE: PRT
<213> ORGANISM: Eupenicillium terrenum

<400> SEQUENCE: 3

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Gly Ala Gly Thr Phe Gln Gln Pro Leu
```

```
            180                 185                 190
Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Glu Pro Asn
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435

<210> SEQ ID NO 4
<211> LENGTH: 1314
<212> TYPE: DNA
<213> ORGANISM: Eupenicillium terrenum

<400> SEQUENCE: 4
atggctcatt cgcgtgcaag caccaaagtc gtcgtggttg ggggaggtgg tacgatcggg      60
tcttcgacgg ctctgcactt aatccgctct ggatataccc cctcaaatat caccgtgctt     120
gacgtataca agacccttc attgcaatct gcaggacatg atttgaacaa gatcatgggc      180 attgattgc gcaacgggcc tgacttgcag ctttcgctgg aatcactcga catgtggcaa     240
aacgatgagt tgttcaagcc attctttcac caagtgggca tgattgattg ttcgtcatcc      300 aaagaggta ttgaaaatct tcgacgaaaa taccagaccc tcctcgatgc gggcattggg      360
ctggagaaga cgaacgtttg gctggaatct gaagatgaga tcctcgccaa agcgccgaat     420 tcacgcgtg aacaagtcaa ggggtggaaa ggcttatttt gcactgatgg aggctggctt     480
gctgcagcca aggctatcaa tgcgatcgga attttcctcc aggacaaagg tgtcaagttt     540
ggctttggag tgctggaac atttcagcaa cctctgttcg ccgctgatgg aaaaaacttgc     600 atcggacttg aaactacaga cggaaccaag tactttgctg acaaggttgt cttggctgct     660
```

```
ggtgcgtgga gtcccacctt ggtggatcta gaagatcagt gtgtttcaaa ggcctgggtt    720
ttcgctcata ttcaactcac acccaaagaa gcggacgcgt acaagaatgt gcctgtggtc    780
tatgatggtg aatatgggtt ctttttttgag cccaacgagt atggggtgat caaagtctgt    840
gacgagttcc ctggtttctc tcgcttcaaa ctgcatcaac cgtacggggc tgcatctccc    900
aagatgatat ccgtaccgcg atcacacgcc aagcatccca cagataccta ccctgatgcc    960
tccgaagtca ccatacgcaa agcgatcgca aggttcctgc agaatttaa agacaaggag    1020 ctcttcaacc gtaccatgtg ctggtgtaca gatacggccg atgctaactt attgatttgc    1080
gaacacccga agtggaagaa tttcattctg gccactggag atagcggaca ttccttcaag    1140
ctgttgccaa acatcgggaa acacgttgtt gagcttttag agggatctct atcgcaggaa    1200
atggctggtg cctggagatg gagacccgga ggtgatgctc ttagatctag acgcggtgct    1260
ccggcaaagg atcttgctga gatgccggga tggaagcatg atgcacattt gtga          1314

<210> SEQ ID NO 5
<211> LENGTH: 23
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (6)..(6)
<223> OTHER INFORMATION: N = ANY ONE NUCLEIC ACID

<400> SEQUENCE: 5
tggytngaya aygargayga rat                                             23

<210> SEQ ID NO 6
<211> LENGTH: 26
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (12)..(12)
<223> OTHER INFORMATION: n = i
<220> FEATURE:
<221> NAME/KEY: misc_feature
<222> LOCATION: (21)..(21)
<223> OTHER INFORMATION: n = i
<220> FEATURE:
<221> NAME/KEY: misc_feature
<222> LOCATION: (24)..(24)
<223> OTHER INFORMATION: n = i

<400> SEQUENCE: 6
ttraarttrt gnccraartc nccngt                                          26

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cccacagaca cttatccaga                                                 20

<210> SEQ ID NO 8
<211> LENGTH: 15
<212> TYPE: DNA
```

```
<213> ORGANISM: ARTIFICIAL SEQUENCE
<220> FEATURE:
<223> OTHER INFORMATION: SYNTHETIC DNA

<400> SEQUENCE: 8
actcagcggc ctctt                                                  15

<210> SEQ ID NO 9
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
agatggtacc aaatattacg ctgacaag                                    28

<210> SEQ ID NO 10
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
tttacaccac gttctttcaa gaactgt                                     27

<210> SEQ ID NO 11
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
aaggcttggg tgtatgctca tattca                                      26

<210> SEQ ID NO 12
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
tccttgtatt tggtcacgtt gaagcaa                                     27

<210> SEQ ID NO 13
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
atgacgtcga atcgtgcaga tac                                         23

<210> SEQ ID NO 14
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
ttacaatttc ggatcatgtt tccat                                       25
```

<210> SEQ ID NO 15
<211> LENGTH: 22
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (3)..(3)
<223> OTHER INFORMATION: n = any nucleic acid
<220> FEATURE:
<221> NAME/KEY: misc_feature
<222> LOCATION: (9)..(9)
<223> OTHER INFORMATION: n = any nucleic acid
<220> FEATURE:
<221> NAME/KEY: misc_feature
<222> LOCATION: (15)..(15)
<223> OTHER INFORMATION: n = any nucleic acid
<220> FEATURE:
<221> NAME/KEY: misc_feature
<222> LOCATION: (21)..(21)
<223> OTHER INFORMATION: n = any nucleic acid

<400> SEQUENCE: 15
acnaaygtnt ggctngarws ng                                    22

<210> SEQ ID NO 16
<211> LENGTH: 19
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (5)..(5)
<223> OTHER INFORMATION: n = any nucleic acid
<220> FEATURE:
<221> NAME/KEY: misc_feature
<222> LOCATION: (8)..(8)
<223> OTHER INFORMATION: n = any nucleic acid
<220> FEATURE:
<221> NAME/KEY: misc_feature
<222> LOCATION: (17)..(17)
<223> OTHER INFORMATION: n = any nucleic acid

<400> SEQUENCE: 16
kccanccngg catytcngc                                        19

<210> SEQ ID NO 17
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
catcccacag atacctaccc t                                     21

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
tcccgatgtt tggcaacagc                                       20

<210> SEQ ID NO 19

```
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gtgcctgtgg tctatgatgg tg                                          22

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
atcaaccgta cggggctgca                                             20

<210> SEQ ID NO 21
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
gatcgcattg atagccttgg c                                           21

<210> SEQ ID NO 22
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
ctccacgcac cagcagccaa gacaaccttg                                  30

<210> SEQ ID NO 23
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
gacatggctc attcgcgtgc aagc                                        24

<210> SEQ ID NO 24
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
caagaatcac aaatgtgcat catgc                                       25
```

FRUCTOSYL PEPTIDE OXIDASE

FIELD OF THE INVENTION

The present invention relates to a novel fructosyl peptide oxidase, to a fructosyl peptide oxidase gene encoding the same, and to a method for producing the novel fructosyl peptide oxidase.

BACKGROUND OF THE INVENTION

Glycated protein is a non-enzymatically-glycated protein, which is produced as a result of covalent bonding between an aldehyde group of sugar, namely, aldose (i.e., a monosaccharide potentially associated with an aldehyde group, and derivatives thereof), and an amino group of a protein. Examples of the amino group of the protein include an N-terminal α-amino group and an internal lysine residue side chain ε-amino group. These glycated proteins are also referred to as Amadori compounds for being formed upon Amadori rearrangement of a Schiff base, a reaction intermediate product.

The glycated proteins are contained in body fluid such as blood in body or in a biological sample such as hair. The concentration of the glycated protein in blood strongly depends on the concentration of saccharide such as glucose dissolved in serum. In diabetic conditions, production of the glycated protein is accelerated. A concentration of glycated hemoglobin in erythrocytes and a concentration of glycated albumin in serum indicate an average blood sugar level for the past predetermined period. Therefore, quantification of the glycated proteins is important for diagnosis and control of the disease process of diabetes.

Examples of known conventional methods for quantifying a glycated protein include, for example, a method employing high-performance liquid chromatography (Chromatogr. Sci., 10, 659 (1979)), a method using a column loaded with a solid material bound with boric acid (Clin. Chem., 28, 2088–2094 (1982)), a method employing electrophoresis (Clin. Chem., 26, 1598–1602 (1980)), a method using antigen-antibody reaction (JJCLA, 18, 620 (1993)), a colorimetric method for determining reducibility using tetrazolium salt (Clin. Chim. Acta, 127, 87–95 (1982)), a calorimetric method using thiobarbituric acid following oxidation (Clin. Chim. Acta, 112, 197–204 (1981)), a method using an enzyme such as glycated amino acid oxidase (Japanese Patent Examined Publication (kokoku) No. 05-33997, Japanese Patent Application Laid-Open (kohyo) No. 11-127895, WO97-13872, Japanese Patent Examined Publication (kokoku) No. 6-65300, and Japanese Patent Applications Laid-Open (kohyo) Nos. 2-195900, 3-155780, 4-4874, 5-192193, 6-46846, 11-155596, 10-313893, 11-504808, 2000-333696, 2001-54398, 2001-204495 and 2001-204494). Furthermore, a new method for quantifying a glycated protein was disclosed recently which is more accurate than any of the above-mentioned methods (Japanese Patent Application Laid-Open (kohyo) No. 2001-95598). According to this quantification method, a sample containing a glycated protein is treated with protease to release a fructosyl peptide from the glycated protein, which is then exposed to oxidase. The resulting product is quantified for quantification of the glycated protein. This method has been recognized as an accurate quantification method that requires short time and simple manipulation.

According to the conventional method using glycated amino acid oxidase, a glycated protein is treated with protease and then the produced glycated amino acid is quantified enzymatically. Specifically, according to this method, a glycated protein is treated with protease or the like to give fructosyl amino acid, which is then exposed to fructosyl amino acid oxidase to quantify the produced hydrogen peroxide. Examples of known fructosyl amino acid oxidases that can be used in such quantification method include oxidase produced by *Corynebacterium* (Japanese Patent Examined Publications (kokoku) Nos. 5-33997 and 6-65300), oxidase produced by *Aspergillus* (Japanese Patent Application Laid-Open (kohyo) No. 3-155780), oxidase produced by *Gibberella* (Japanese Patent Application Laid-Open (kohyo) No. 7-289253), oxidase produced by *Fusarium* (Japanese Patent Applications Laid-Open (kohyo) Nos. 7-289253 and 8-154672), oxidase produced by *Penicillium* (Japanese Patent Application Laid-Open (kohyo) No. 8-336386), oxidase produced by *Tricosporon* (Japanese Patent Application Laid-Open (kohyo) No. 2000-245454), and ketoamine oxidase (Japanese Patent Application Laid-Open (kohyo) No. 5-192193). However, while these enzymes act well on fructosyl amino acids, they do not act on fructosyl peptides. Oxidase produced by *E. coli* DH5α (pFP1) (FERM BP-7297) described in Japanese Patent Application Laid-Open (kohyo) No. 2001-95598 is known as an enzyme that acts on fructosyl peptide. However, preparing a quantification kit with this enzyme is difficult since its basic physicochemical properties are unknown and it has poor stability.

The objective of the present invention is to provide a novel and stable fructosyl peptide oxidase, a fructosyl peptide oxidase gene encoding the same, and a method for producing the novel fructosyl peptide oxidase.

SUMMARY OF THE INVENTION

The present inventors have devoted themselves to solving the above-described problems and found that various microorganisms obtained by searching widely in nature produce novel fructosyl peptide oxidases which have superior stability. The present inventors have succeeded in acquiring these enzymes, found that these fructosyl peptide oxidases have various novel physicochemical properties that are advantageous for quantifying glycated proteins, and succeeded in isolating fructosyl peptide oxidase genes, thereby achieving the present invention.

Thus, the present invention relates to a fructosyl peptide oxidase which acts on fructosyl valyl histidine in the presence of oxygen and catalyzes a reaction that produces (α-ketoaldehyde, valyl histidine and hydrogen peroxide. The present invention also relates to a fructosyl peptide oxidase which catalyzes the above-mentioned reaction and whose remaining activity following a heat treatment at 45° C. for 10 minutes is 80% or higher, and to a fructosyl peptide oxidase which catalyzes the above-mentioned reaction and whose molecular weight is about 52,000 (SDS-PAGE). Moreover, the present invention relates to a fructosyl peptide oxidase which catalyzes the above-mentioned reaction, whose remaining activity following a heat treatment at 45° C. for 10 minutes is 80% or higher, and whose molecular weight is about 52,000 (SDS-PAGE).

Furthermore, the present invention relates to a fructosyl peptide oxidase having the following physicochemical properties.

(a) Action and substrate specificity: Acts on fructosyl valyl histidine in the presence of oxygen and catalyzes a reaction that produces α-ketoaldehyde, valyl histidine and hydrogen peroxide.

(b) Optimal pH: pH 6.0–8.0.

(c) Temperature range suitable for action: 20–45° C.

(d) Thermostability: a remaining activity of 80% or higher following a heat treatment at 45° C. for 10 minutes.

(e) Stable pH range: pH 6.0–9.0.

(f) Molecular weight: about 52,000 (SDS-PAGE).

The present invention also relates to a method for producing the fructosyl peptide oxidase, the method comprising: culturing, in a medium, a filamentous fungus capable of producing the above-mentioned fructosyl peptide oxidase or a filamentous fungus selected from the group consisting of *Achaetomiella, Achaetomium, Thielavia, Chaetomium, Gelasinospora, Microascus, Coniochaeta* and *Eupenicillium* which are capable of producing the above-mentioned fructosyl peptide oxidases; and collecting the fructosyl peptide oxidase from the culture.

The present invention further relates to a fructosyl peptide oxidase which catalyzes the above-mentioned reaction and which acts on fructosyl valyl histidine but has less action on F-fructosyl lysine, to the same fructosyl peptide oxidase whose remaining activity following a heat treatment at 45° C. for 10 minutes is 80% or higher, and to the same fructosyl peptide oxidase having the following physicochemical properties:

(a) optimal pH: pH 6.0–8.0;

(b) temperature range suitable for action: 20–40° C.;

(c) thermostability: a remaining activity of 80% or higher following a heat treatment at 45° C. for 10 minutes; and (d) stable pH range: pH 6.0–9.0.

The present invention also relates to a method for producing the fructosyl peptide oxidase, the method comprising: culturing, in a medium, a filamentous fungus capable of producing the above-mentioned fructosyl peptide oxidase or a filamentous fungus that belongs to *Eupenicillium* or *Coniochaeta* which is capable of producing the above-mentioned fructosyl peptide oxidase; and collecting the fructosyl peptide oxidase from the culture.

The present invention further relates to any of the following proteins (a), (b) and (c) having a fructosyl peptide oxidase activity:

(a) a protein comprising an amino acid sequence represented by SEQ ID NO: 1;

(b) a protein comprising an amino acid sequence having deletion, substitution and/or addition of one to several amino acids relative to the amino acid sequence represented by SEQ ID NO: 1, and having a fructosyl peptide oxidase activity; and (c) a protein having 80% or higher homology with the amino acid sequence represented by SEQ ID NO: 1, and having a fructosyl peptide oxidase activity.

The present invention further relates to a gene coding for any of the following proteins (a), (b) and (c) having a fructosyl peptide oxidase activity:

(a) a protein comprising an amino acid sequence represented by SEQ ID NO: 1;

(b) a protein comprising an amino acid sequence having deletion, substitution and/or addition of one to several amino acids relative to the amino acid sequence represented by SEQ ID NO: 1, and having a fructosyl peptide oxidase activity; and (c) a protein having 80% or higher homology with the amino acid sequence represented by SEQ ID NO: 1, and having a fructosyl peptide oxidase activity.

The present invention also relates to a gene comprising any of the following DNAs (a), (b) and (c):

(a) DNA comprising a nucleotide sequence represented by SEQ ID NO: 2;

(b) DNA which hybridizes under stringent conditions with DNA comprising a nucleotide sequence complementary to a full-length or 15 or more consecutive bases of the DNA comprising the nucleotide sequence represented by SEQ ID NO: 2, and which codes for a protein having a fructosyl peptide oxidase activity; and (c) DNA which has 80% or higher homology with a full-length or 15 or more consecutive bases of the DNA comprising the nucleotide sequence represented by SEQ ID NO: 2, and which codes for a protein having a fructosyl peptide oxidase activity.

The present invention further relates to recombinant DNA obtained by inserting the above-mentioned gene into vector DNA.

The present invention further relates to a transformant or a transductant comprising the above-mentioned recombinant DNA.

The present invention also relates to a method for producing a fructosyl peptide oxidase, comprising: culturing the above-mentioned transformant or transductant in a medium; and collecting the fructosyl peptide oxidase from the culture.

The present invention further relates to any of the following proteins (a), (b) and (c) having a fructosyl peptide oxidase activity:

(a) a protein comprising an amino acid sequence represented by SEQ ID NO: 3;

(b) a protein comprising an amino acid sequence having deletion, substitution and/or addition of one to several amino acids relative to the amino acid sequence represented by SEQ ID NO: 3, and having a fructosyl peptide oxidase activity; and (c) a protein having 80% or higher homology with the amino acid sequence represented by SEQ ID NO: 3, and having a fructosyl peptide oxidase activity.

The present invention further relates to a gene coding for any of the following proteins (a), (b) and (c) having a fructosyl peptide oxidase activity:

(a) a protein comprising an amino acid sequence represented by SEQ ID NO: 3;

(b) a protein comprising an amino acid sequence having deletion, substitution and/or addition of one to several amino acids relative to the amino acid sequence represented by SEQ ID NO: 3, and having a fructosyl peptide oxidase activity; and (c) a protein having 80% or higher homology with the amino acid sequence represented by SEQ ID NO: 3, and having a fructosyl peptide oxidase activity.

The present invention also relates to a gene comprising any of the following DNAs (a), (b) and (c):

(a) DNA comprising a nucleotide sequence represented by SEQ ID NO: 4;

(b) DNA which hybridizes under stringent conditions with DNA comprising a nucleotide sequence complementary to a full-length or 15 or more consecutive bases of the DNA comprising the nucleotide sequence represented by SEQ ID NO: 4, and which codes for a protein having a fructosyl peptide oxidase activity; and (c) DNA which has 80% or higher homology with a full-length or 15 or more consecutive bases of the DNA comprising the nucleotide sequence represented by SEQ ID NO: 4, and which codes for a protein having a fructosyl peptide oxidase activity.

The present invention further relates to recombinant DNA obtained by inserting the above-mentioned gene into vector DNA.

The present invention further relates to a transformant or a transductant comprising the above-mentioned recombinant DNA.

The present invention also relates to a method for producing a fructosyl peptide oxidase, comprising: culturing the above-mentioned transformant or transductant in a medium; and collecting the fructosyl peptide oxidase from the culture.

DESCRIPTION OF THE PREFERRED EMBODIMENTS

Figure 1:
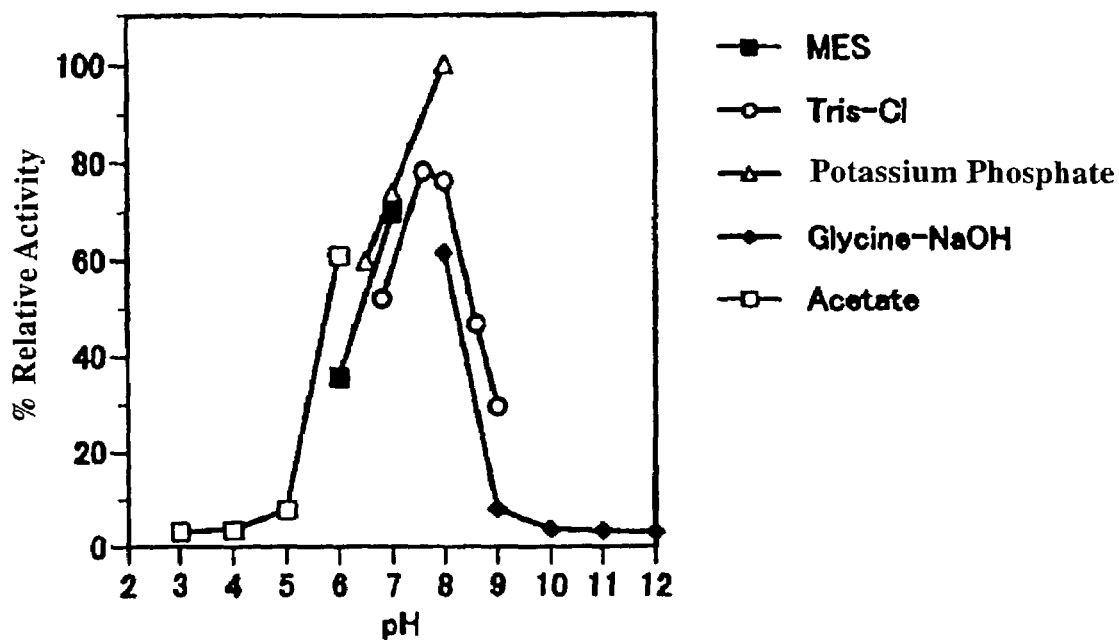
FIG. 1 shows the optimum pH for the inventive oxidase produced by a filamentous fungus belonging to *Achaetomiella*.

Hereinafter, the present invention will be described in more detail. The fructosyl peptide oxidases according to the present invention (hereinafter, referred to as "the oxidases of the invention") are oxidases which act on fructosyl valyl histidine in the presence of oxygen and catalyze the following reaction formula that results in α-ketoaldehyde, valyl histidine and hydrogen peroxide. Any oxidase with this action is considered as the oxidase of the invention.

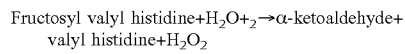

Fructosyl valyl histidine+$H_2O$+$_2$→α-ketoaldehyde+ valyl histidine+$H_2O_2$

Any oxidase that catalyzes the above-mentioned reaction is contemplated as the present invention (and referred to as "the oxidase of the invention"), including, for example, oxidases that act on other fructosyl amino acids such as $N^\epsilon$-fructosyl lysine (ε-fructosyl lysine) and N-fructosyl glycine (fructosyl glycine), and oxidases that act on various fructosyl peptides. On the other hand, fructosyl peptide oxidases that act on fructosyl valyl histidine but have less action on ε-fructosyl lysine (referred to as "the oxidases of the invention that have less action on ε-fructosyl lysine") refer to the oxidases of the invention which catalyze the above-mentioned reaction formula and which have a lower activity upon use of ε-fructosyl lysine substrate as compared to the activity upon use of fructosyl valyl histidine substrate, and may be any oxidase which can accurately quantify fructosyl valyl histidine in a sample containing ε-fructosyl lysine. The oxidases of the invention which do not act on ε-fructosyl lysine are also contemplated as the present invention. The oxidases of the invention that have less action on ε-fructosyl lysine are particularly preferable for quantifying fructosyl valyl histidine in a biological sample containing ε-fructosyl lysine.

In addition, some embodiments of the oxidases of the invention may comprise: a fructosyl peptide oxidase with a molecular weight of about 52,000 (SDS-PAGE) which catalyzes the above-mentioned reaction; a fructosyl peptide oxidase which catalyzes the above-mentioned reaction and whose remaining activity following a heat treatment at 45° C. for 10 minutes is 80% or higher; and a fructosyl peptide oxidase with a molecular weight of about 52,000 (SDS-PAGE) which catalyzes the above-mentioned reaction and whose remaining activity following a heat treatment at 45° C. for 10 minutes is 80% or higher. Furthermore, the oxidase of the invention may also comprise a fructosyl peptide oxidase which catalyzes the above-mentioned reaction and at the same time has any or a combination of the following physicochemical properties (a) to (e).

(a) Optimal pH: pH 6.0–8.0

For example, 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) and 200 mM glycine buffer (pH 8.0–12.0) are used as buffers to perform enzyme reactions at the indicated pH at 30° C., thereby determining optimal pH. For example, the oxidases of the invention may have an optimal pH at 5.0–9.0, preferably pH 6.0–8.0.

(b) Temperature Range Suitable for Action: 20–45° C.

For example, a reaction solution having the same composition as that of a reaction solution used for the activity assay described later is used to determine activities of the enzyme at various temperatures, thereby determining a suitable temperature range for action. The oxidases of the invention may, for example, have a suitable temperature range of 20–50° C., preferably 25–45° C.

(c) Thermostability: a remaining activity of 80% or higher following a heat treatment at 45° C. for 10 minutes.

For example, 200 mM potassium phosphate buffer (pH 8.0) is used for a treatment at 45° C. for 10 minutes to determine the remaining activities of the oxidases of the invention. The oxidases of the invention having high stability at a high temperature range are particularly preferable for industrial use. The oxidases of the invention may, for example, have a remaining activity of 50% or higher, preferably 70% or higher, and more preferably 80% or higher under the above-described conditions.

(d) Stable pH range: pH 6.0–9.0

For example, 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) and 200 mM glycine buffer (pH 8.0–12.0) are used as buffers to perform enzyme reactions at the indicated pH at 30° C. for 10 minutes, thereby determining the remaining activities of the oxidases of the invention. For example, the oxidases of the invention may have a stable pH at 5.0–10.0, preferably at 6.0–9.0.

(e) Molecular weight: about 52,000 (SDS-PAGE)

For example, the molecular weight is determined by SDS-PAGE technique using Multigel 10/20 (Daiichi Pure Chemicals Co., Ltd.). The oxidases of the invention may have a molecular weight of 45,000–60,000, preferably 47,000–57,000 (SDS-PAGE). Presently, SDS-PAGE technique is a general technique frequently used for determining the molecular weight of a protein. Considering the possible error of the molecular weight determined by this determination method, the molecular weight of about 52,000 (SDS-PAGE) is considered to cover molecular weights within a range of 47,000 to 57,000.

On the other hand, the oxidases of the invention that have less action on ε-fructosyl lysine refer to the oxidases of the invention which have a lower activity upon use of ε-fructosyl lysine substrate as compared to the activity upon use of fructosyl valyl histidine substrate, and may be any oxidase which can accurately quantify fructosyl valyl histidine in a sample containing ε-fructosyl lysine. Specifically, if an activity of the oxidases of the invention that have less action on ε-fructosyl lysine is defined as 100 upon use of fructosyl valyl histidine substrate, an activity upon use of ε-fructosyl lysine substrate is 70 or less, preferably 50 or less, more preferably 20 or less.

Embodiments of the oxidases of the invention that have less action on ε-fructosyl lysine may comprise: a fructosyl peptide oxidase which catalyzes the above-mentioned reaction and which acts on fructosyl valyl histidine but acts less on ε-fructosyl lysine, and whose remaining activity following a heat treatment at 45° C. for 10 minutes is 80% or higher; and a fructosyl peptide oxidase which has the above action and properties as well as any or a combination of the following physicochemical properties (a) to (d).

(a) Optimal pH: pH 6.0–8.0

For example, 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) and 200 mM glycine buffer (pH 8.0–12.0) are used as buffers to perform enzyme reactions at the indicated pH at 30° C., thereby determining optimal pH. For example, the oxidases of the invention that have less action on ε-fructosyl lysine may have an optical pH at 5.0–9.0, preferably at 6.0–8.0.

(b) Temperature range suitable for action: 20–40° C.

For example, a reaction solution having the same composition as that of a reaction solution for the activity assay described later is used to determine activities of the enzyme at various temperatures, thereby determining a suitable temperature range. The oxidases of the invention that have less action on ε-fructosyl lysine may, for example, have a suitable temperature range of 20–50° C., preferably 25–40° C.

(c) Thermostability: a remaining activity of 80% or higher following a heat treatment at 45° C. for 10 minutes For example, 200 mM potassium phosphate buffer (pH 8.0) is used for a treatment at 45° C. for 10 minutes. Then, the remaining activities of the enzymes of the invention are determined. The oxidases of the invention having high stability at a high temperature range are particularly preferable for industrial use. The oxidases of the invention that have less action on ε-fructosyl lysine may, for example, have a remaining activity of 50% or higher, preferably 70% or higher, more preferably 80% or higher under the above-described conditions.

(d) Stable pH range: pH 6.0–9.0

For example, 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) and 200 mM glycine buffer (pH 8.0–12.0) are used as buffers to perform enzyme reactions at the indicated pH at 30° C. for 10 minutes, thereby determining the remaining activities of the oxidases of the invention. For example, the oxidases of the invention that have less action on ε-fructosyl lysine may have a stable pH range at 5.0–10.0, preferably at 6.0–9.0.

Enzyme activities of the oxidase of the invention and the oxidase of the invention that have less action on ε-fructosyl lysine (hereinafter, the term "the oxidases of the invention" may comprise both the oxidase of the invention and the oxidase of the invention that have less action on ε-fructosyl lysine) may principally be determined by determining the amount of α-ketoaldehyde, peptide, hydrogen peroxide or the like which are produced through enzyme reaction or by determining the amount of oxygen consumed by the enzyme reaction. Hereinafter, a method for determining the amount of hydrogen peroxide will be described as one example. Unless otherwise noted, fructosyl valyl histidine is used as a substrate for determining the activities of the oxidases of the invention. Titer of the enzyme is defined such that an amount of enzyme for producing 1 μmol hydrogen peroxide per minute is 1 U as determined using a fructosyl valyl histidine substrate.

A. Preparation of Reagents (1) Reagent 1: POD-4-AA solution 1.0 kU of peroxidase (Toyobo Co., Ltd, TYPE III) and 100 mg of 4-aminoantipyrine (Tokyo Kasei Kogyo Co., Ltd.) are dissolved in 0.1 M potassium phosphate buffer (pH 8.0) to a constant volume of 1 L.

(2) Reagent 2: 2,4-dichlorophenol sulfate solution 25 ml of a commercially available 2% solution (available from Nacalai Tesque, Inc.) is dissolved in ion exchange water to a constant volume of 100 ml.

(3) Reagent 3: substrate solution (150 mM; final concentration 5 mM)

624 mg of fructosyl valyl histidine is dissolved in ion exchange water to a constant volume of 10 ml. Alternatively, fructosyl glycine or ε-fructosyl lysine of 357 mg or 462 mg, respectively, may be dissolved in ion exchange water to a constant volume of 10 ml to be used as a substrate. Fructosyl valine histidine was prepared as described in Japanese Patent Application Laid-Open (kohyo) No. 2001-95598. Fructosyl glycine and ε-fructosyl lysine were prepared according to a method of Horiuchi et al. (Agric. Biol. Chem., 53, 103–110, 1989; Agric. Biol. Chem., 55, 333–338, 1991).

B. Determination Assay 2.7 ml of Reagent 1, 100 μl of Reagent 2 and 100 μl of enzyme solution are mixed and pre-heated at 30° C. for 5 minutes. Then, 100 μl of Reagent 3 is added and thoroughly mixed to determine absorbance at 510 nm using a spectrophotometer (U-2000A, Hitachi, Ltd.). Measurement values indicate changes in the absorbance per minute at 510 nm after 1 to 3 minutes. A control solution was prepared in the same manner as described above except 100 μl ion exchange water was added instead of 100 μl Reagent 3. A standard solution of hydrogen peroxide and ion exchange water were used instead of Reagent 3 and the enzyme solution, respectively, to prepare a graph showing relationship with respect to the level of color. Referring to this graph, micromole of hydrogen peroxide produced per minute at 30° C. is calculated and used as the unit for expressing the activity of the enzyme solution. The presence of action on ε-fructosyl lysine can be determined in the same manner by using Reagent 3 (substrate solution) containing ε-fructosyl lysine substrate instead of fructosyl valyl histidine substrate.

Thus, the oxidases of the invention comprise oxidase that acts on fructosyl valyl histidine in the presence of oxygen and catalyzes reaction represented by the above-described formula which results in α-ketoaldehyde, valyl histidine and hydrogen peroxide. Such oxidases of the invention may, for example, have the above-described behavior and any or a combination of the above-described physicochemical properties. Such oxidases of the invention act efficiently upon free fructosyl valyl histidine resulting from protease treatment of a sample containing a glycated protein such as glycated hemoglobin, and thus can be used as an effective enzyme for quantifying the glycated protein. The oxidases of the invention having high thermostability are particularly preferable for use as a clinical diagnostic enzyme.

When a sample containing a glycated protein is treated with protease, ε-fructosyl lysine may also be released together with fructosyl valyl histidine depending on the sample used. In this case, when the amount of fructosyl valyl histidine is determined with the oxidase of the invention which acts well on ε-fructosyl lysine, accurate determination may be difficult. In such case, the oxidase of the invention that has less action on ε-fructosyl lysine is more preferable.

The oxidases of the invention can be acquired from nature by conducting searches of enzymes derived from microorganisms, animals and plants. For example, in order to search for microorganisms capable of producing the oxidases of the invention, microorganisms are cultured in media supplied with an enzyme-producing inducer such as fructosyl valyl histidine. The obtained microorganism cells are disrupted to test for fructosyl peptide oxidase activities using fructosyl valyl histidine as a substrate. Thus, microorganisms capable of producing the oxidases of the invention can be obtained. The microorganisms used here may be newly isolated from soil, or obtained from a microorganism collection organization or the like. Furthermore, in order to obtain the oxidases of the invention with superior storage stability, solutions containing the disrupted microorganism cells obtained as described above may be subjected to a heat treatment, for example, at 45° C. for 10 minutes, after which activities are determined and those with higher remaining activities are selected. As organisms capable of producing the oxidases of the invention, in terms of easy handling, productivity and the like, for example, microorganisms are preferable, particularly filamentous fungi that belong to genus such as *Achaetomiella, Achaetomium, Thielavia, Chaetomium, Gelasinospora, Microascus, Coniochaeta* and *Eupenicillium*. Preferable microorganisms may be filamentous fungi belonging to *Achaetomiella, Chaetomium, Coniochaeta* and *Eupenicillium*, particularly microorganisms such as *Achaetomiella virescens* ATCC 32393, *Chaetomium* sp. NISL 9335 (FERM BP-7799), *Coniochaeta* sp. NISL 9330 (FERM BP-7798) and *Eupenicillium terrenum* ATCC 18547.

In order to search for microorganisms capable of producing the oxidases of the invention that act on fructosyl valyl histidine but have less action on ε-fructosyl lysine, microorganisms capable of producing the oxidases of the invention which have lower activity upon use of ε-fructosyl lysine substrate as compared to the activity upon use of fructosyl valyl histidine substrate are selected from the microorganisms capable of producing the oxidases of the invention obtained by the above-described search. As microorganisms capable of producing the oxidases of the invention that have less action on ε-fructosyl lysine, filamentous fungi are preferable, such as those that belong to *Eupenicillium* and *Coniochaeta*. Preferable filamentous fungi are, for example, *Eupenicillium terrenum* ATCC 18547, *Eupenicillium senticosum* IFO 9158, *Eupenicillium idahoense* IFO 9510, *Eupenicillium euglaucum* IFO 31729 and *Coniochaeta* sp. NISL 9330 (FERM BP-7798).

The oxidases of the invention are obtained not only by modifying native oxidases of the invention by techniques such as gene engineering or mutation process but also by modifying conventionally known enzyme genes such as fructosyl amino acid oxidase genes.

Examples of such modification techniques include, for example, irradiating organisms capable of producing the above-described oxidases with UV ray, X-ray, radiation or the like, or bringing organisms capable of producing the above-described oxidases into contact with a mutagen such as ethylmethanesulfonate, N-methyl-N'-nitro-N-nitrosoguanidine or nitrous acid, thereby obtaining a microorganism that produces modified oxidase of the invention. Then, from the obtained microorganism, the oxidase of the invention can be obtained. In general, gene engineering can be employed to modify genes encoding oxidases with different properties so as to obtain the oxidases of the invention.

Hereinafter, a method for producing the oxidases of the invention will be described. According to the present invention, the oxidases of the invention are collected and produced from organisms having activities of the oxidases of the invention, according to a variety of generally employed methods for isolating proteins. For example, a preferable method for producing the present oxidase comprises culturing a microorganism capable of producing the above-described oxidase of the invention in a medium, and collecting from the culture a protein having a fructosyl peptide oxidase activity or a protein having a fructosyl peptide oxidase activity but having less action on ε-fructosyl lysine. Specifically, as an example, the following method may be employed which uses a microorganism capable of producing the oxidase of the invention.

First, searched microorganisms that are found to produce the oxidases of the invention (collectively referred to as "the microorganisms") are cultured. The microorganisms may be cultured by a solid culture method but more preferably by a liquid culture method. As the media for culturing the above-mentioned microorganisms, one or more types of inorganic salts such as potassium dihydrogenphosphate, dipotassium hydrogenphosphate, magnesium sulfate, ferric chloride, ferric sulfate and manganese sulfate, and, if necessary, sugars, vitamins or the like, are added to one or more types of nitrogen sources such as infusions of yeast extract, peptone, meat extract, corn steep liquor, soybean or wheat malt. As an enzyme inducible substrate, an enzyme substrate such as fructosyl glycine, fructosyl valyl histidine, ε-fructosyl lysine or the like may appropriately be added to increase the yield.

Initial pH of the medium may suitably be adjusted to 7 to 9. Preferably, culture is performed at 25–42° C., preferably at about 30° C., for 1 to 5 days by submerged aeration culture, shake culture, standing culture or the like. Following culture, the oxidases of the invention may be collected from the cultures with generally employed enzyme collecting means.

Specifically, cells are separated from the culture solutions, for example, by filtration, centrifugation or the like and then washed. The oxidases of the invention are preferably collected from these cells. These cells can be used directly. However, it is more preferable to disrupt the cells with disrupting means such as an ultrasonic homogenizer, a French Press, a Dynomill and the like, disrupt the cells by lysing cell walls of the cells with a cell wall lytic enzyme such as lysozyme, or extract the enzymes from the cells by using a surfactant such as Triton X-100 so as to collect the oxdases of the invention from these cells.

A general enzyme purification method may be employed to purify and isolate the oxidases of the invention from the obtained crude enzyme solutions. Preferably, a combination of, for example, ammonium sulfate salting out method, organic solvent precipitation, ion exchange chromatography, gel filtration chromatography, hydrophobic chromatography, absorption chromatography, electrophoresis and the like may be performed. Thus, the oxidases of the invention may be isolated until a generally single band appears on SDS-PAGE. The above-mentioned purification methods can suitably be combined to prepare enzyme preparations with different degrees of purification according to use. The oxidases of the invention that have less action on ε-fructosyl lysine may also be produced according to a method similar to the above-described method for producing the oxidases of the invention.

The produced oxidases of the invention may effectively be used for quantifying a glycated protein as described below. First, a glycated protein such as $HbA_{1c}$ is digested by protease such as Molsin, AO-protease, peptidase (available from Kikkoman Corp.), carboxypeptidase Y or Protin P (available from Daiwa Fine Chemicals Co., Ltd.) to release fructosyl peptide. Then, the released fructosyl valyl histidine is quantified with the oxidase of the invention. When ε-fructosyl lysine which is also released at the same time causes a problem, an enzyme that acts on ε-fructosyl lysine, for example, fructosyl amino acid oxidase derived from fungus (Japanese Patent Applications Laid-Open (kohyo) Nos. 7-289253, 8-154672, 8-336386, etc.) or fructosyl amine oxidase (Japanese Patent Application Laid-Open (kohyo) No. 03-155780) may be used to digest the ε-fructosyl lysine. Subsequently, fructosyl valyl histidine can be quantified with the oxidase of the invention. Alternatively, an oxidase of the invention that has less action on ε-fructosyl lysine may be used so that fructosyl valyl histidine can accurately be quantified without digesting the released ε-fructosyl lysine.

The oxidases of the invention may comprise the following oxidase (a), (b), (c), (d), (e) or (f):

(a) a fructosyl peptide oxidase comprising an amino acid sequence represented by SEQ ID NO: 1;

(b) a fructosyl peptide oxidase comprising an amino acid sequence having deletion, substitution and/or addition of one to several amino acids relative to the amino acid sequence represented by SEQ ID NO: 1;

(c) a fructosyl peptide oxidase comprising an amino acid sequence having 80% or higher homology with the amino acid sequence represented by SEQ ID NO: 1;

(d) a fructosyl peptide oxidase comprising an amino acid sequence represented by SEQ ID NO: 3;

(e) a fructosyl peptide oxidase comprising an amino acid sequence having deletion, substitution and/or addition of one to several amino acids relative to the amino acid sequence represented by SEQ ID NO: 3; and (f) a fructosyl peptide oxidase comprising an amino acid sequence having 80% or higher homology with the amino acid sequence represented by SEQ ID NO: 3.

Herein, "deletion, substitution and/or addition of one to several amino acids" means deletion, substitution and/or addition of, for example, 1 to 20, preferably 1 to 10, and more preferably 1 to 5 amino acids.

Herein, "having 80% or higher homology" has no limitation as long as homology with the amino acid sequence represented by SEQ ID NO: 1 or 3 is 80% or higher, for example, 80% or higher, preferably 90% or higher, and most preferably 95% or higher.

The above-described oxidases of the invention may be obtained by cloning and expressing a native fructosyl peptide oxidase gene derived from chromosomal DNA or cDNA of *Coniochaeta* sp. NISL 9330 (FERM BP-7798) or a native fructosyl peptide oxidase gene derived from *Eupenicillium terrenum* ATCC 18547 in a suitable vector host system. The oxidases of the invention may also be obtained from fructosyl peptide oxidase derived from various sources acquired from nature.

The fructosyl peptide oxidase genes (hereinafter, referred to as "the genes of the invention") coding for the fructosyl peptide oxidases of the invention may comprise genes coding for the oxidases of the invention (a) to (f) above, and genes coding for the oxidases of the invention comprising the following DNA (g), (h), (i), (j), (k) or (l):

(g) DNA comprising a nucleotide sequence represented by SEQ ID NO: 2;

(h) DNA which hybridizes with DNA comprising a nucleotide sequence complementary to a full-length or 15 or more consecutive bases of the DNA comprising the nucleotide sequence represented by SEQ ID NO: 2 under stringent conditions, and which codes for a protein having a fructosyl peptide oxidase activity;

(i) DNA which indicates 80% or higher homology with a full-length or 15 or more consecutive bases of the DNA comprising the nucleotide sequence represented by SEQ ID NO: 2, and which codes for a protein having a fructosyl peptide oxidase activity;

(j) DNA comprising a nucleotide sequence represented by SEQ ID NO: 4;

(k) DNA which hybridizes with DNA comprising a nucleotide sequence complementary to a full-length or 15 or more consecutive bases of the DNA comprising the nucleotide sequence represented by SEQ ID NO: 4 under stringent conditions, and which codes for a protein having a fructosyl peptide oxidase activity; and (l) DNA which indicates 80% or higher homology with a full-length or 15 or more consecutive bases of the DNA comprising the nucleotide sequence represented by SEQ ID NO: 4, and which codes for a protein having a fructosyl peptide oxidase activity.

Herein, "stringent conditions" refer to conditions under which a signal from a specific hybrid is clearly distinguished from a signal from a non-specific hybrid upon colony hybridization, plaque hybridization, Southern blot hybridization or the like (Current Protocols in Molecular Biology (WILEY, Interscience, 1989)). These conditions differ depending on the hybridization system used as well as the type, sequence and length of the probe. These conditions can be determined by changing the hybridization temperature, washing temperature and salt concentration. For example, when a signal from a non-specific hybrid is positively detected, the hybridization and washing temperatures can be raised while the salt concentration is decreased, thereby enhancing specificity. When a signal from a specific hybrid is not detected, the hybridization and washing temperatures can be decreased while the salt concentration is increased, thereby stabilizing the hybrid. More specifically, DNA that is subjected to hybridization under stringent conditions may have a certain homology with a nucleotide sequence of probe DNA. Homology as used in "DNA comprising a nucleotide sequence indicating 80% or higher homology with a full-length or 15 or more consecutive bases of a nucleotide sequence" refers to a homology of, for example, 80% or higher, preferably 90% or higher, and most preferably 95% or higher.

Genes coding for the above-mentioned oxidases of the invention may be, for example, a gene coding for an oxidase obtained by cloning and expressing a native fructosyl peptide oxidase gene derived from chromosomal DNA or cDNA of *Coniochaeta* sp. NISL 9330 (FERM BP-7798) in a suitable vector host system, or a gene coding for an oxidase obtained by cloning and expressing a native fructosyl peptide oxidase gene derived from chromosomal DNA or cDNA of *Eupenicillium terrenum* ATCC 18547 in a suitable vector host system.

The above-mentioned DNA may be, for example, a native fructosyl peptide oxidase gene derived from chromosomal DNA or cDNA of *Coniochaeta* sp. NISL 9330 (FERM BP-7798), or a native fructosyl peptide oxidase gene derived from chromosomal DNA or cDNA of *Eupenicillium terrenum* ATCC 18547. The genes coding for the oxidases of the invention or the DNA thereof may also be obtained from fructosyl peptide oxidases derived from various sources acquired from nature.

In addition, the oxidases of the invention, genes coding for the oxidases of the invention or DNA thereof may also be obtained from various mutant fructosyl peptide oxidases obtained from native fructosyl peptide oxidases.

Hereinafter, a method for obtaining the genes of the invention will be described.

In order to obtain the genes of the invention, a generally employed gene cloning method is used. For example, chromosomal DNA or mRNA is extracted from cells capable of producing the above-described oxidases of the invention according to a routine method (e.g., a method described in Current Protocols in Molecular Biology (WILEY, Interscience, 1989)). Moreover, cDNA can be synthesized using mRNA as a template. Thus, chromosomal DNA or a cDNA library can he obtained. Next, suitable probe DNA is synthesized based on the amino acid sequence of the oxidase of the invention, which is used to screen for DNA from the chromosomal DNA or cDNA library. Alternatively, DNA containing a gene fragment of interest is amplified by polymerase chain reaction (PCR method) such as the 5'-RACE or 3'-RACE method by producing suitable primer DNA based on the above-mentioned amino acid sequence. Then, the obtained DNA fragments are linked to obtain DNA containing a full-length gene of the invention. Furthermore, the genes of the invention coding for the oxidases of the invention can be obtained from various organisms through hybridization with the above-mentioned probe DNA.

For example, the genes of the invention from *Coniochaeta* sp. NISL 9330 (FERM BP-7798) or *Eupenicillium terrenum* ATCC 18547 can be obtained as follows.

First, the above-described microorganism is cultured. The obtained cells are frozen in liquid nitrogen, followed by physical disruption using, for example, a mortar. From the obtained fine powdery cell debris, chromosomal DNA is extracted according to a general method using a commercially available DNA extraction kit or the like. Then, a total RNA fraction is extracted from the cell debris according to a general method by using a commercially available RNA extraction kit or the like. Then, RNA is collected from this extract through ethanol precipitation. If necessary, a commercially available Oligo dT column is used to fractionate RNA having a poly-A chain according to a general method.

Next, the oxidase of the invention produced from the above-mentioned microorganism is purified, isolated and sequenced to determine the N-terminal amino acid sequence thereof. The obtained peptide fragment is digested with trypsin or lysyl-end peptidase to give a peptide fragment, and the amino acid sequence thereof (i.e., the internal amino acid sequence) is determined. Then, considering the information of the obtained partial amino acid sequence and the codon usage frequency of the above-mentioned microorganism, primers are synthesized for PCR. These primers as well as the obtained chromosomal DNA or RNA as a template are used to perform PCR or RT-PCR, thereby obtaining a DNA fragment coding for a part of the oxidase of the invention. Furthermore, primers are appropriately synthesized based on the nucleotide sequence of the obtained DNA fragment.

Next, using the above-mentioned primers and RNA, cDNA containing the fragment of the present gene is amplified by a suitable RT-PCR method such as the 5'-RACE or 3'-RACE method. The amplified products are linked to obtain cDNA containing a full-length gene of the invention. RT-PCR using the RNA as a template and synthesized primers complementary to the 5'- and 3'-terminal sequences can amplify cDNA containing the present gene.

The amplified DNA can be cloned following a general method. The amplified DNA is inserted into a suitable vector to obtain recombinant DNA. For cloning, a commercially available kit such as TA Cloning Kit (available from Invitrogen), plasmid vector DNA such as pUC119 (available from Takara Bio Inc.), pBR322 (available from Takara Bio Inc.), pMAL-C2 (available from New England Labs), pBluescript II SK$^+$ (available from Stratagene) and pKK223-3 (available from Amersham Bioscience K.K.), bacteriophage vector DNA such as λENBL3 (available from Stratagene) and λDASH II (available from Funakoshi Co., Ltd.), and the like can be used.

The thus-obtained recombinant DNA is used to transform or transduce, for example, *E. coli* K12, preferably *E. coli* JM109 (available from Toyobo Co., Ltd.), DH5α (available from Toyobo Co., Ltd.), XL1-Blue (available from Funakoshi Co., Ltd.) and the like, thereby obtaining a transformant or a transductant containing the recombinant DNA. Transformation can be performed, for example, according to the method by D. M. Morrison (Methods in Enzymology, 68, 326–331, 1979). Transduction can be performed, for example, according to the method by B. Hohn (Methods in Enzymology, 68, 299–309, 1979). As a host cell, microorganisms other than *E. coli,* for example, other bacteria, yeasts, filamentous fungi or actinomycetes, or animal cells may be used.

The total nucleotide sequence of the above-described amplified DNA may be analyzed by using, for example, LI-COR MODEL 4200L sequencer (LI-COR, Inc.) or 370A DNA sequence system (Perkin Elmer). The nucleotide sequence is compared with information of the partial amino acid sequences so as to confirm whether or not the present gene is obtained. By analyzing the obtained gene of the invention, the translated polypeptide, namely, the amino acid sequence of the oxidase of the invention, is determined.

Examples of the genes of the invention include genes containing DNA comprising a nucleotide sequence represented by SEQ ID NO: 2 or 4. Plasmid pKK223-3-CFP containing DNA comprising a nucleotide sequence represented by SEQ ID NO: 2 was deposited at the International Patent Organism Depositary, the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan as FERM BP-8132, while plasmid puc-EFP containing DNA comprising a nucleotide sequence represented by SEQ ID NO: 4 was deposited at the AIST as FERM BP-8131.

The above-mentioned genes of the invention may be modified to give various modified oxidases of the invention.

In order to modify the above-mentioned genes, any known method may be used, for example, a method in which the above-mentioned recombinant DNA is brought into contact with a chemical mutation agent such as hydroxylamine or nitrous acid, a point mutation method for random modification using a PCR method, a well-known site-directed mutagenesis for site-specific substitution or deletion using a commercially available kit, a method in which the recombinant DNA is selectively cleaved, a selected oligonucleotide is then removed from or added thereto, followed by linking (i.e., an oligonucleotide mutagenesis method). Then, the treated recombinant DNA is purified using desalting column, QIAGEN (available from Qiagen) or the like to obtain various recombinant DNAs.

Through these modifications, for example, the following genes can be obtained: the genes of the invention containing DNA which hybridizes under stringent conditions with DNA comprising a nucleotide sequence complementary to a full-length or 15 or more consecutive bases of the DNA comprising the nucleotide sequence represented by SEQ ID NO: 2 or 4 and which codes for a protein having a fructosyl peptide oxidase activity; or the genes of the invention containing DNA which indicates 80% or higher homology with a full-length or 15 or more consecutive bases of the DNA comprising the nucleotide sequence represented by SEQ ID NO: 2 or 4, and which codes for a protein having a fructosyl peptide oxidase activity.

Furthermore, by modifying the genes of the invention, for example, the following oxidases of the invention can be obtained: a protein comprising an amino acid sequence having deletion, substitution and/or addition of one to several amino acids relative to the amino acid sequence represented by SEQ ID NO: 1 or 3, and having a fructosyl peptide oxidase activity; or a protein having 80% or higher homology with the amino acid sequence represented by SEQ ID NO: 1 or 3, and having a fructosyl peptide oxidase activity.

Next, the transformant or transductant including the above-described recombinant DNA is cultured in a medium, and fructosyl peptide oxidase is collected from the culture. In general, the transformant or transductant is cultured by using a medium suitable for growing a host used. For example, when *E. coli* is used as a host, the transformant is seeded in 10L LB medium, and cultured using a jar fermenter at 30° C. for 24 hours with an air flow of 1 L/min and an agitation rate of 600 rpm. The obtained 10 L culture is centrifuged at 7,000 rpm for 10 minutes, thereby collecting and obtaining cells. From the obtained cells, the enzyme of the invention can be obtained according to the above-described methods.

EXAMPLES

Hereinafter, the present invention will be described in more detail with reference to the Experimental Example and Examples described below, although the technical scope of the present invention is not limited to these Examples.

Experimental Example 1

Search for Microorganism Capable of Producing the Inventive Oxidase

Soil-derived microorganisms and deposited microorganisms provided by microorganism collection organizations were used for the search. Soil-derived microorganisms were isolated from about 100 soil samples obtained at different places in and around Noda-City (Chiba) and Tsukuba-City (Ibaraki). Particularly, one small spatula of each soil sample was grown by shake-culture on a enrichment medium (0.5% yeast extract, 0.2% potassium dihydrogenphosphate, 0.05% magnesium sulfate, 0.1% fructosyl valyl histidine, pH 6.5) at 30° C. for one day, and microorganisms were isolated on a plate medium (enrichment medium+1.2% agar). About 5,000 strains were isolated, most of which were bacteria and yeast. Deposited strains used included 380 strains of yeast, 480 strains of filamentous fungi and 700 strains of actinomycetes.

Soil-derived bacteria and yeast were inoculated on 3 ml of the above-described enrichment medium, filamentous fungi were inoculated on 3 ml of enzyme inducible medium 1 (0.1% yeast extract, 0.1% malt extract, 0.1% potassium dihydrogenphosphate, 0.05% magnesium sulfate, 0.1% fructosyl valyl histidine, pH 7.3) and actinomycetes were inoculated on 3 ml of enzyme-induction media 2 (0.2% dry yeast, 1.25% soybean powder, 2% fructosyl valyl histidine). Soil-derived microorganisms were grown by shake-culture for 24 hours while yeast, filamentous fungi and actinomycetes were grown by shake-culture for 3–5 days at 30° C. Each culture solution was centrifuged at 3,000 rpm for 10 minutes to obtain cells. Next, cells were suspended in a lysis buffer (100 mM phosphate buffer (pH 8), 1 mM EDTA, 1 mg/ml lysozyme, 0.5 mM PMSF), disrupted by, for example, ultrasonication (1–3 minutes) or using a Physcotron (50 power, 30 seconds, twice, available from Microtec Nition Co., Ltd.), added with Triton X-100 to a final concentration of 0.5%, and centrifuged at 15,000 rpm, 4° C. for 10 minutes to collect supernatant as crude enzyme solution. Each of the crude enzyme solutions obtained was examined for the presence or absence of fructosyl peptide oxidase activity by the above-described activity assay to select 19 strains with the same activity, all of which were filamentous fungi. Particularly, these filamentous fungi included *Achaetomiella* (1 strain), *Achaetomium* (8 strains), *Thielavia* (1 strain), *Chaetomium* (2 strains), *Gelasinospora* (1 strain), *Microascus* (1 strain), *Coniochaeta* (1 strain), and *Eupenicillium* (4 strains).

Example 1

Preparing the Inventive Oxidase Produced by the Filamentous Fungus Belonging to the Genus *Achaetomiella*

*Achaelomiella virescens* ATCC 32393 was inoculated on 0.05 L of a medium (0.4% yeast extract, 1% malt extract, 2% glucose, 0.1% tryptone, 0.1% potassium dihydrogenphosphate, 0.05% magnesium sulfate, pH 7) contained in a 0.15

L Erlenmeyer flask, and grown by rotary shaking culture at 120 rpm, 30° C. for 3 days. Next, the culture solution (seed) was dispensed (10 mL/flask) into 5 L Erlenmeyer flasks (each containing 1 L of the above-described medium) and grown by rotary shaking culture at 90 rpm, 30° C. for 4 days. Cells were collected from the culture solution using a Buchner funnel with a filter. The cells obtained were frozen for storage at −80° C.

Frozen cells (collected from 6 L of culture solution) were suspended in 1 L of buffer A (0.4 M sodium chloride, 20 mM phosphate buffer, 1 mM EDTA, 5% glycerol, 0.5 mM PMSF, pH 8), and disrupted by a French press. Solution containing disrupted cells was centrifuged at 9,000 rpm for 15 minutes, and supernatant was loaded on a DEAE Sepharose FF (available from Amersham Biotech) column (5 cm×18 cm) pre-equilibrated with buffer A. Additionally, 500 ml of buffer A was added, and the whole elution solution was collected. The elution solution was added slowly with ammonium sulfate to 40% saturation to precipitate an excess amount of protein. The solution was left to stand at 4° C. overnight, and then centrifuged at 9,000 rpm, 4° C. for 15 minutes. Next, ammonium sulfate was added slowly to supernatant to 65% saturation to precipitate the protein of interest. The supernatant solution was left to stand at 4° C. overnight, and centrifuged at 9,000 rpm, 4° C. for 15 minutes to collect precipitant.

The precipitant was dissolved in 30 ml of buffer B (10 mM Tris-HCl, 0.2 mM EDTA, 1% glycerol, pH 8.6), desalted with PD-10 (available from Amersham Biotech), and then applied to a Q Sepharose FF (available from Amersham Biotech) column (2.5 cm×15 cm) pre-equilibrated with buffer B. The gel was washed with 150 ml of buffer B and eluted with a linear gradient from buffer B to buffer C (150 mM sodium chloride, 50 mM Tris-HCl, 1 mM EDTA, 5% glycerol, pH 8.6). Active fraction was eluted at about 0.08 M sodium chloride.

The eluted active fraction was concentrated in CentriPrep 10 (available from Amicon), dialyzed, and loaded on TSK gel super Q (available from Tosoh Co., Ltd.). Elution was performed using a linear gradient from buffer B to buffer C. Activity was monitored at 280 nm using a flow rate of 1 ml/min. Active fraction was eluted at about 0.08 M sodium chloride.

The active fraction obtained was concentrated in Microcon 10 (available from Amicon), and loaded on a POROS PE (available from Perceptive Biosystems). Elution was performed using a linear gradient from buffer D (2 M ammonium sulfate, 20 mM phosphate buffer, 1 mM EDTA, 5% glycerol, pH 7) to buffer E (20 mM phosphate buffer, 1 mM EDTA, 5% glycerol, pH 8). Activity was monitored at 280 nm using a flow rate of 2 ml/min. Active fraction was eluted at about 1 M ammonium sulfate. The active fraction obtained was analyzed by SDS-PAGE to obtain a single band (molecular weight=about 52,000). The active fraction obtained was used to determine the following physiochemical properties.

Example 2

Physiochemical Properties of the Inventive Oxidase Produced by Filamentous Fungus Belonging to the Genus *Achaetomiella*

Figure 3:
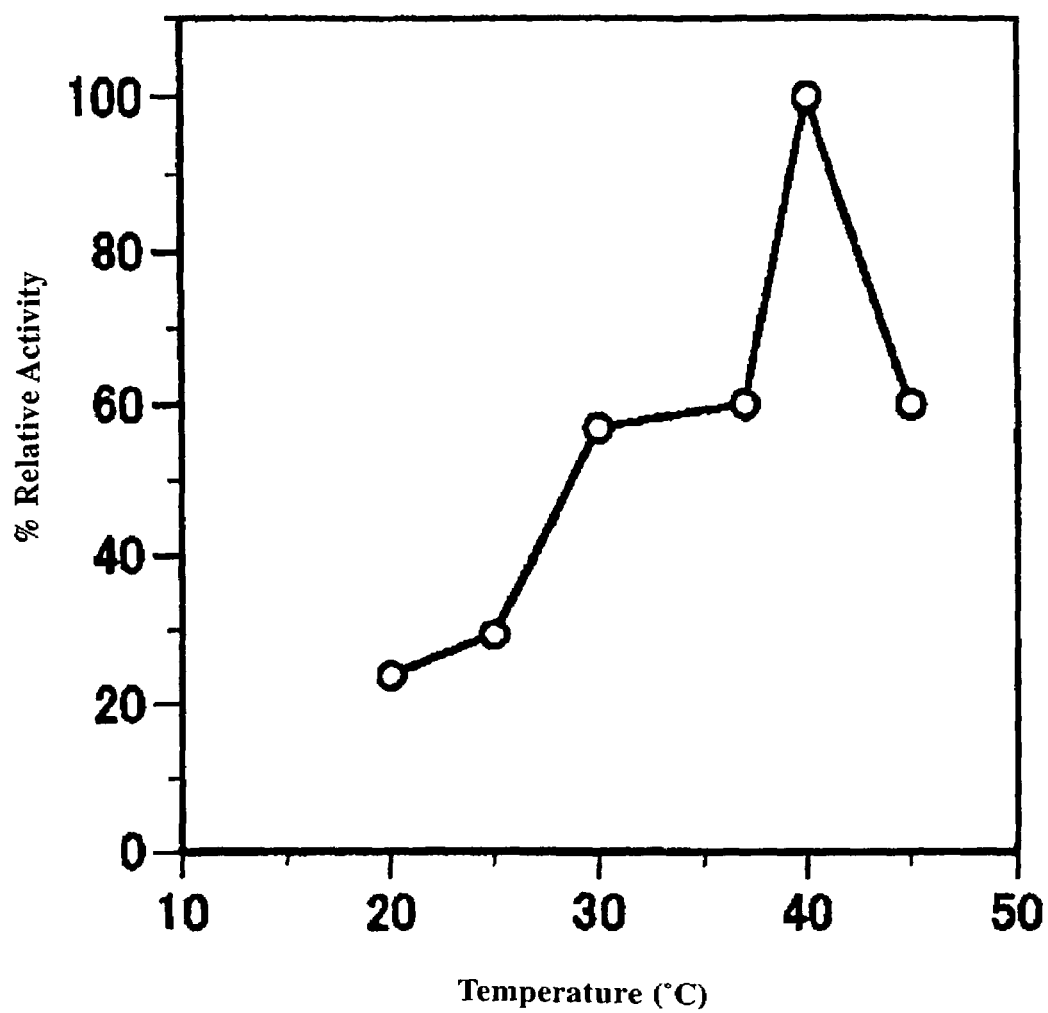
FIG. 3 shows the optimum temperature range for the inventive oxidase produced by a filamentous fungus belonging to *Achaetomiella*.

The physiochemical properties of the inventive oxidase obtained in Example 1 will be described below.
(a) Activity and substrate specificity The activity of the inventive oxidase was assayed by the above-described enzyme activity assay using, as substrate, fructosyl valyl histidine, fructosyl glycine or ε-fructosyl lysine. The inventive oxidase had 42% relative activity for fructosyl valyl histidine and 18% for fructosyl glycine when compared to 100% activity for ε-fructosyl lysine.
(b) Optimum pH Enzyme reaction was monitored in 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. The results are shown in FIG. 1. The inventive oxidase exhibited its maximum activity (100%) at pH 8.0 and relative activities of 70% or higher at pH 7.0–8.0. From these results, the optimum pH for the inventive oxidase was determined to be pH 7.0–8.0, and most preferably pH 8.0.
(c) Km value for fructosyl valyl histidine In the above-described activity assay, the activity of the oxidase was monitored using different concentrations of fructosyl valyl histidine (substrate), and Michaelis constant (Km) was determined from a Lineweaver-Burk plot. The Km value for fructosyl valyl histidine was found to be 2.3 mM.
(d) Optimum temperature range The activity of the inventive oxidase was assayed at different temperatures using reactions which consisted of the same compositions as those used in the above-described activity assay. The results are shown in FIG. 3. The enzyme exhibited its maximum activity (100%) at around 40° C. and relative activities of 50% or higher at from 30 to 45° C.

Figure 2:
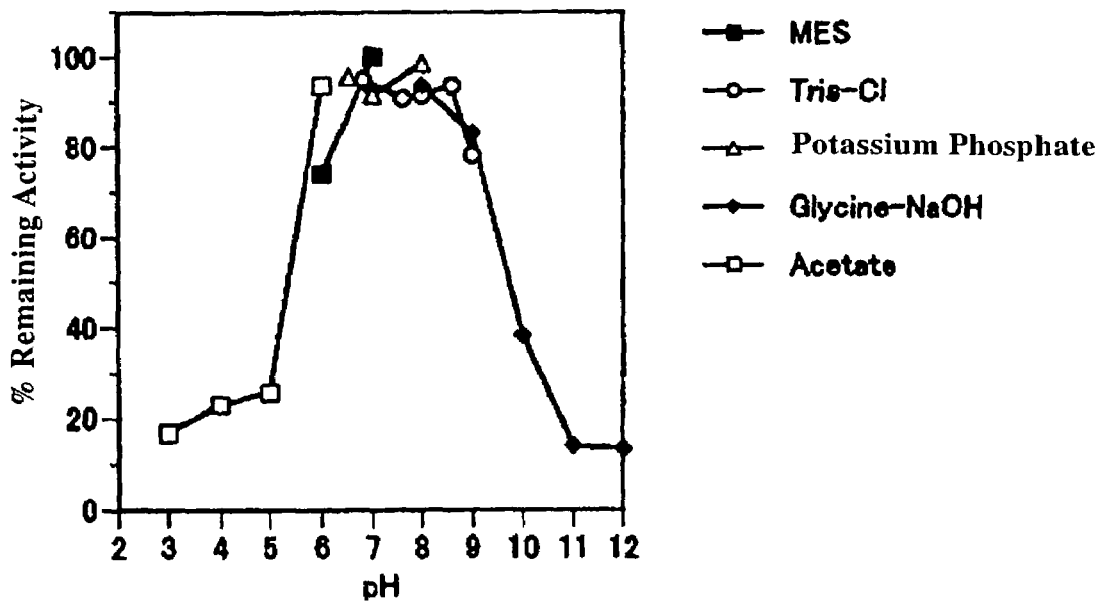
FIG. 2 shows the stable pH range for the inventive oxidase produced by a filamentous fungus belonging to *Achaetomiella*.
Figure 4:
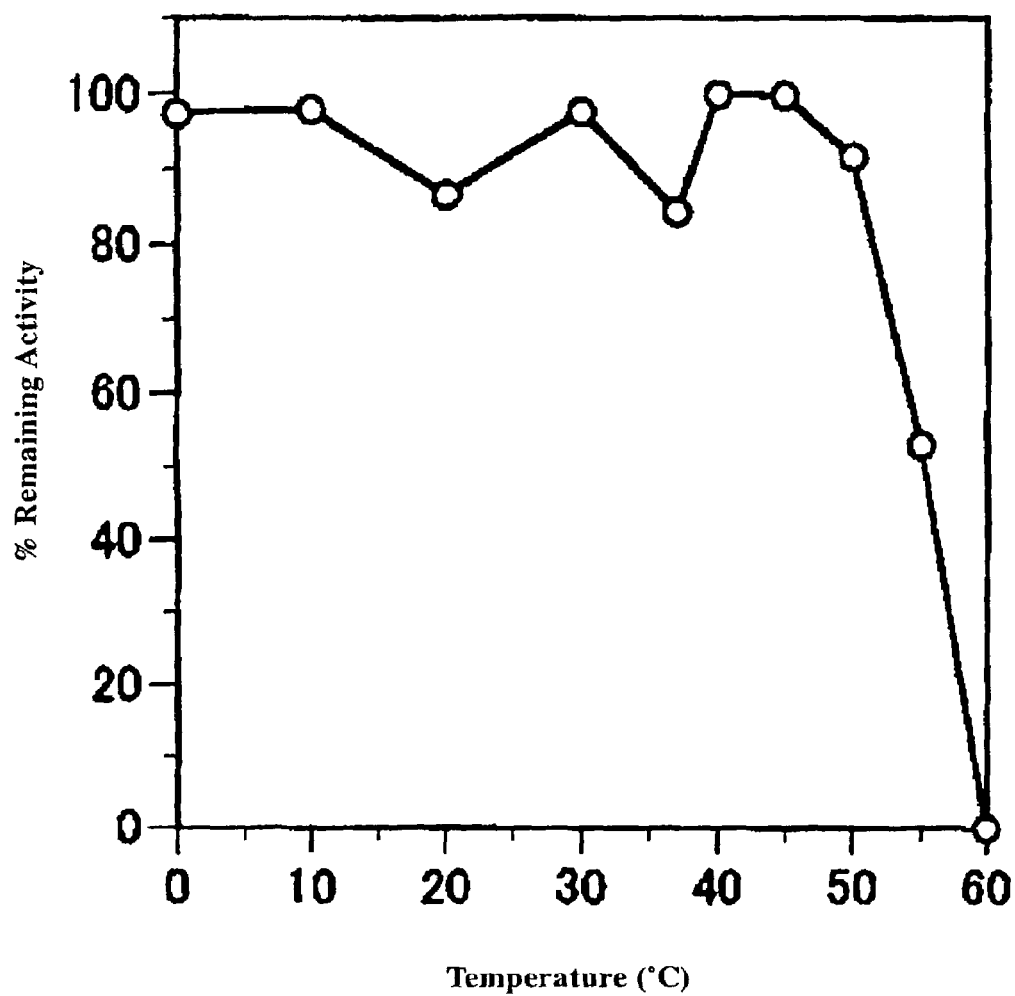
FIG. 4 shows the thermostability of the inventive oxidase produced by a filamentous fungus belonging to *Achaetomiella*.

From these results, the optimum temperature range of the inventive oxidase was determined to be 30–45° C.
(e) Thermostability The thermostability of the inventive oxidase following a treatment with 200 mM potassium phosphate buffer (pH 8.0) at different temperatures for 10 minutes is shown in FIG. 4 which illustrates that the inventive oxidase remained stable up to about 50° C.
(f) Stable pH range The inventive oxidase was treated with 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. for 10 minutes, and its remaining activity was determined. The results are shown in FIG. 2. The inventive oxidase exhibited its maximum activity (100%) at around pH 7.0 and remaining activities of 70% or higher at pH 6.0–9.0.

From these results, the stable pH range for the inventive oxidase was determined to be pH 6.0–9.0.
(g) Molecular weight Molecular weight was determined by SDS-PAGE on Multigel 10/20 (available from DAIICHI PURE CHEMICALS CO., LTD.). The molecular weight of the inventive oxidase was determined to be about 52,000.
(h) Identifying reaction product Reaction solution was assayed by HPLC to identify reaction products. First, 50 μl of reaction solution (2 mM fructosyl valyl histidine, 5 mM phosphate buffer (pH 8.0), 0.003 U of the inventive oxidase) was incubated at 37° C. for 2 hours, diluted (10×) and then assayed for the reaction products in a TSK gel Amide-80 column (available from Tosoh Co., Ltd.). As a control, the same procedure was repeated except for using a buffer instead of the enzyme. As a result, a peak was detected only for fructosyl valyl histidine in the control case, while in the enzyme case a peak was detected only for valyl histidine and no peak was detected for fructosyl valyl histidine. From these results, it was confirmed that the inventive oxidase catalyzes the decomposition of fructosyl valyl histidine to produce valyl histidine. Further, it was suggested that this reaction cleaved an α-ketoamine bond, as in the glycated amino acid oxidase reaction.

Example 3

Comparison of Thermostability

The thermostability of the inventive oxidase produced by the filamentous fungus belonging to the genus *Achaetomiella* was compared to that of the oxidase disclosed in Japanese Patent Application Laid-Open (kohyo) No. 2001-95598. *E. coli* strain DH5α (pFP1) (FERM BP-7297) which produces the oxidase disclosed in Japanese Patent Application Laid-Open (kohyo) No. 2001-95598 was inoculated on 10ml of LB-amp medium (1% bactotryptone, 0.5% bacto-yeast extract, 0.5% sodium chloride, 50 µg/mL ampicillin, pH 7), and grown by reciprocal shaking culture at 120 rpm, 30° C. for 20 hours. The resultant culture solution was centrifuged at 12,000 rpm for 10 minutes to collect cells which were then suspended in 10 ml of lysis buffer (50 mM phosphate buffer, 1 mM EDTA, 5% glycerol, 0.5 mM PMSF, pH 8), and then disrupted by ultrasonication. The suspension containing disrupted cells was centrifuged at 12,000 rpm for 10 minutes and supernatant obtained was used as crude enzyme solution. The crude enzyme solution was treated with 200 mM potassium phosphate buffer (pH 8.0) at 45° C. for 10 minutes, and then assayed for its activity using fructosyl valyl histidine as the substrate. No activity was detected. These results show that the oxidase disclosed in Japanese Patent Application Laid-Open (kohyo) No. 2001-95598 exhibited a low thermostability, which is disadvantageous in that it may not be stable during storage when it is formulated into a reagent (an enzyme) contained in a kit for clinical diagnosis. On the other hand, the inventive oxidase exhibited, as described above, an extremely high thermostability with 80% or higher activity following a heat treatment at 45° C. for 10 minutes.

Example 4

The Inventive Oxidases Produced by Filamentous Fungi

Among the filamentous fungi obtained in the search described in Experimental Example 1 above, the above-listed filamentous fungi, *Achaetomiella* (1 strain), *Achaetomium* (8 strains), *Thielavia* (1 strain), *Chaetomium* (2 strains), *Gelasinospora* (1 strain), *Microascus* (1 strain), *Coniochaeta* (1 strain) and *Eupenicillium* (1 strain) were used to produce the inventive oxidases. Next, the physiochemical properties of these oxidases were determined. The results are shown in Tables 1 and 2. Each of these 16 strains was cultured on 3 ml of the above-described enzyme inducible medium 1 at 30° C. for 4 days and cells were then collected. The cells collected were suspended in 0.9 ml of lysis buffer, disrupted by using a Physcotron and by ultrasonication, added with Triton X-100 to a final concentration of 0.5%, and then centrifuged at 15,000 rpm, 4° C. for 10 minutes to collect supernatant which was then used as crude enzyme sample. Each of the crude enzyme samples obtained was examined for its activity for fructosyl valyl histidine (FVH), fructosyl glycine (FG) or ε-fructosyl lysine (FFL).

For comparison, activities of each enzyme are shown as % relative activities when compared to its activity for ε-fructosyl lysine (100%). Each crude enzyme sample was heat-treated at 45° C. for 10 minutes, and then its activity for fructosyl valyl histidine was determined and compared to the activity before treatment. As shown in Tables 1 and 2, all of these sample strains showed activities on fructosyl valyl histidine though with different levels of activity per medium. Although these samples obtained from different strains exhibited slightly different substrate specificities, the inventive oxidases produced by *Eupenicillium terrenum* ATCC 18547 and *Coniochaeta* sp. NISL 9330 (FERM BP-7798) exhibited particularly preferable properties in that they acted well on fructosyl valyl histidine but less on ε-fructosyl lysine. It was found that the inventive oxidases produced by *Achaetomiella virescens* ATCC 32393 and *Chaetomium* sp. NISL 9335 (FERM BP-7799) exhibit a relatively strong action on fructosyl valyl histidine. It was also shown that under the above-described heat-treatment conditions, the inventive oxidase samples produced by 12 out of 16 strains exhibited remaining activities of 100% or higher while those produced by the remaining 4 strains exhibited 80–100% remaining activities, which indicated that all of the oxidase samples produced by those 16 strains had extremely high stability.

TABLE 1

| Strain | Activity per medium (U/L) | Substrate specificity (% relative activity) | | | Thermo-stability (%) |
|---|---|---|---|---|---|
| | | FVH | FG | εFL | |
| *Thielavia novoquineensis* NISL 9334 | 0.9 | 17 | 10 | 100 | 100 |
| *Chaetomium quatrangulatum* NISL 9329 | 1.0 | 8 | 15 | 100 | 107 |
| *Achaetomium luteum* ATCC 18524 | 1.6 | 39 | 22 | 100 | 100 |
| *Achaetomium strumarium* NISL 9324 | 1.1 | 26 | 21 | 100 | 100 |
| *Achaetomium globosum* NISL 9321 | 4.1 | 18 | 10 | 100 | 104 |
| *Achaetomium luteum* NISL 9323 | 7.2 | 38 | 18 | 100 | 108 |
| *Gelasinospora pseudo-reticulata* NISL 9332 | 1.2 | 17 | 14 | 100 | 102 |

TABLE 2

| Strain | Activity per medium (U/L) | Substrate specificity (% relative activity) | | | Thermo-stability (%) |
|---|---|---|---|---|---|
| | | FVH | FG | εFL | |
| *Achaetomiella virescens* ATCC 32393 | 11.6 | 71 | 25 | 100 | 88 |
| *Achaetomium strumarium* NISL 9325 | 20.9 | 42 | 24 | 100 | 107 |
| *Achaetomium strumarium* NISL 9326 | 6.0 | 15 | 6 | 100 | 102 |
| *Achaetomium* sp. NISL 9327 | 3.2 | 26 | 21 | 100 | 104 |
| *Chaetomium* sp. NISL 9335 | 13.2 | 69 | 88 | 100 | 100 |
| *Eupencillium terrenum* ATCC 18547 | 2.8 | 1023 | 1862 | 100 | 100 |
| *Microascus* sp. NISL 9333 | 19.1 | 27 | 37 | 100 | 94 |
| *Achaetomium* sp. NISL 9328 | 19.4 | 38 | 21 | 100 | 80 |

TABLE 2-continued

| Strain | Activity per medium (U/L) | Substrate specificity (% relative activity) | | | Thermo-stability (%) |
|---|---|---|---|---|---|
| | | FVH | FG | εFL | |
| Coniochaeta sp. NISL 9330 | 70.1 | 165 | 65 | 100 | 80 |

Example 5

Preparing the Inventive Oxidases Produced by Linear Fungi Belonging to the Genera *Chaetomium* and *Coniochaeta*

*Chaetomium* sp. NISL 9335 (FERM BP-7799) and *Coniochaeta* sp. NISL 9330 (FERM BP-7798) cells were cultured, and the inventive oxidases were purified therefrom. Both oxidases were obtained using the same purification procedure.

Each of the oxidases obtained was inoculated on 3 ml of a medium (0.4% yeast extract, 1% malt extract, 2% glucose, 0.1% tryptone, 0,1% potassium dihydrogenphosphate, 0,05% magnesium sulfate, pH 7) contained in a glass tube (1.6 cm (diameter)×12.5 cm), and grown by reciprocal shaking culture at 120 rpm, 30° C. for 1 day. Then, 3 ml of the culture (seed) was dispensed (3 ml/flask) into 1 L Erlenmeyer flasks each containing 0.4 L of the above-described medium, and grown by rotary shaking culture at 130 rpm, 30° C. for 4 days. Cells were collected from the culture solution by filtration using a Buchner funnel with a filter or by centrifugation at 12,000 rpm for 10 minutes. The cells obtained were frozen for storage at −80° C.

Frozen cells (collected from 0.4 L of culture solution) were suspended in 0.025 L of buffer A, and disrupted by a French press. The suspension containing disrupted cells was centrifuged at 12,000 rpm for 10 minutes, and ammonium sulfate was added slowly to the supernatant to 65% saturation to precipitate the protein of interest. The supernatant solution was left to stand at 4° C. overnight, and centrifuged at 12,000 rpm for 10 minutes to collect precipitant.

The precipitant was then dissolved in 5 ml of buffer D and centrifuged at 15,000 rpm for 10 minutes to give a supernatant which was then subjected to POROS PE. Elution was performed using a linear gradient from buffer D to buffer E. Activity was monitored at 280 nm using a flow rate of 2ml/min. Active fractions were eluted at about 0.25 M ammonium sulfate for both of the enzymes. Both of the active fractions obtained were concentrated and demineralized in Microcon 10 (available from Amicon) and used to determine their physiochemical properties as described below.

Example 6

The Physiochemical Properties of the Inventive Oxidase Produced by *Chaetomium* sp.

Figure 5:
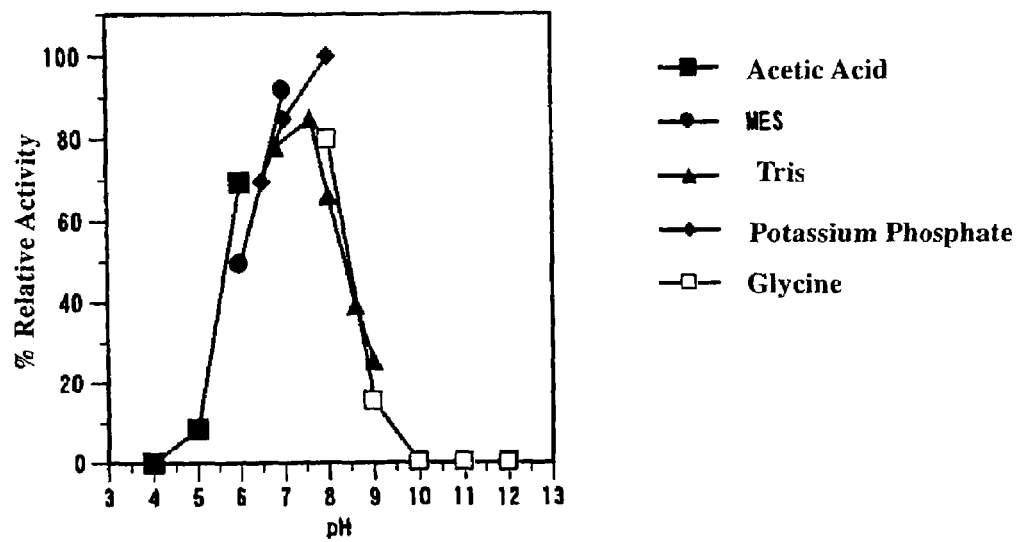
FIG. 5 shows the optimum pH for the inventive oxidase produced by a filamentous fungus belonging to *Chaetomium*.
Figure 7:
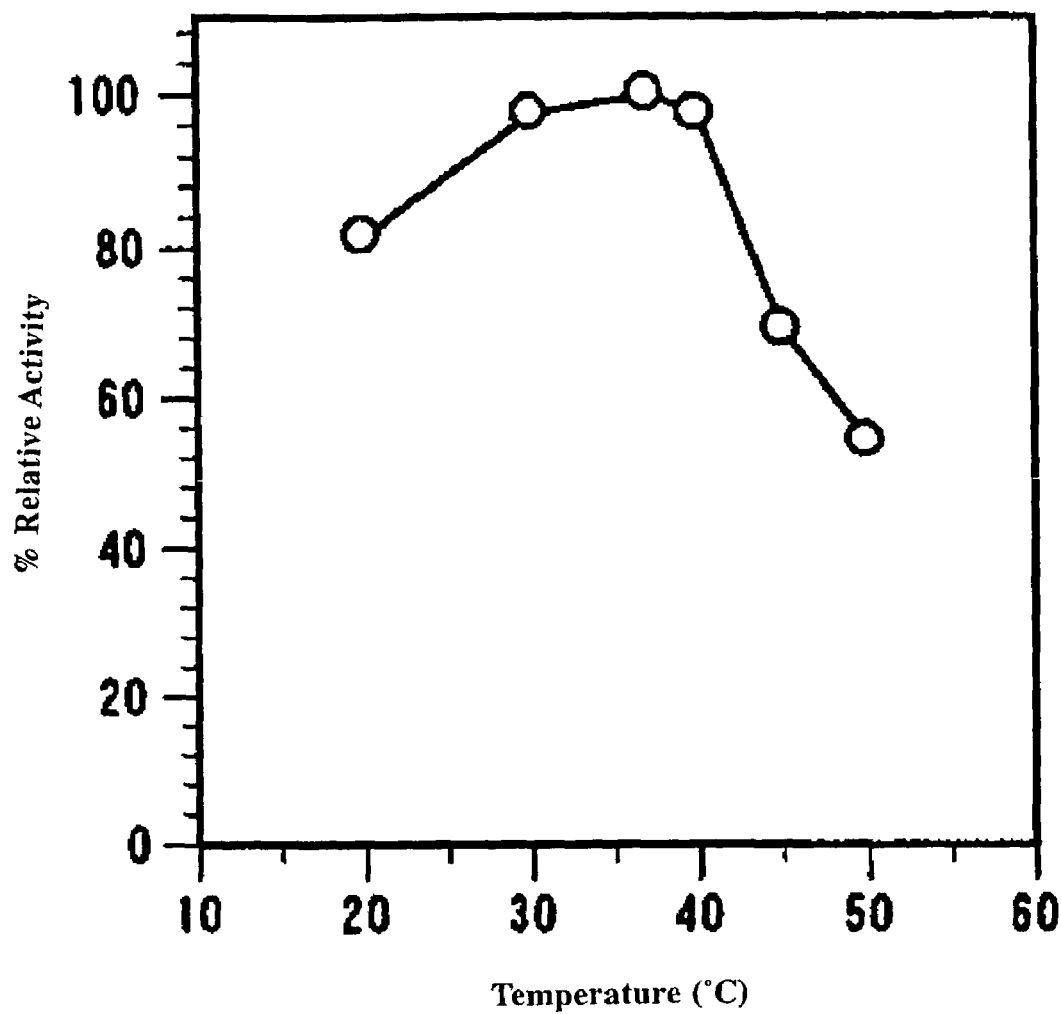
FIG. 7 shows the optimum temperature range for the inventive oxidase produced by a filamentous fungus belonging to *Chaetomium*.

The physiochemical properties of the inventive oxidase produced by *Chaetomium* sp. NISL 9335 (FERM BP-7799) obtained in Example 5 will be described below.
(a) Activity and substrate specificity The activity of the inventive oxidase was assayed by the above-described enzyme activity assay using, as substrate, fructosyl valyl histidine, fructosyl glycine or ε-fructosyl lysine. The inventive oxidase exhibited 40% relative activity for fructosyl valyl histidine and 28% for fructosyl glycine when compared to 100% activity for ε-fructosyl lysine.
(b) Optimum pH Enzyme reaction was monitored in 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. The results are shown in FIG. 5. The inventive oxidase exhibited its maximum activity at pH 8.0. It still exhibited relative activities of 70% or higher at pH 6.0–8.0 when compared to the maximum activity (100%) at around pH 8.0. From these results, the optimum pH for the inventive oxidase was determined to be pH 6.0–8.0, and most preferably pH 8.0.
(c) Optimum temperature range The activity of the inventive oxidase was assayed at different temperatures using reaction solutions which consisted of the same compositions as those used in the above-described activity assay. The results are shown in FIG. 7. The enzyme exhibited its maximum activity (100%) at around 37° C. and relative activities of 60% or higher at from 20 to 45° C.

Figure 6:
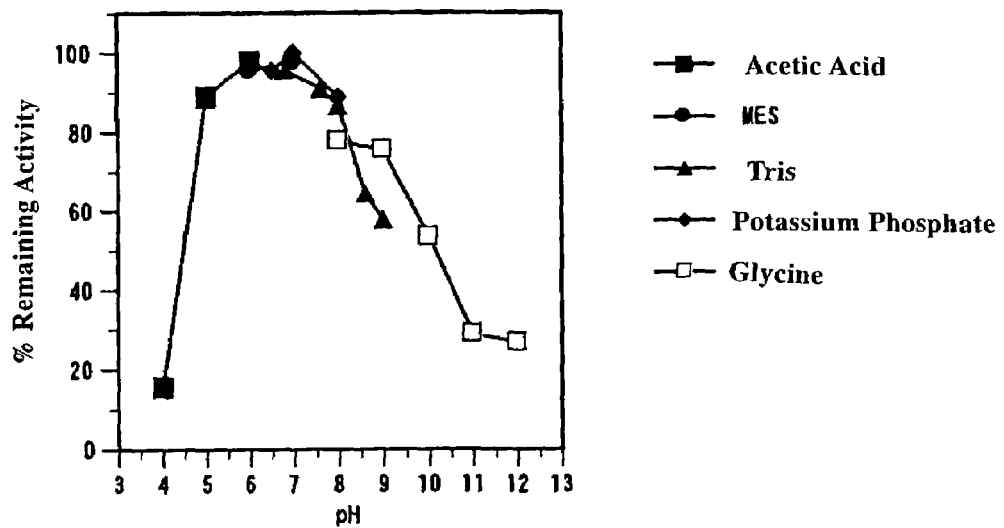
FIG. 6 shows the stable pH range for the inventive oxidase produced by a filamentous fungus belonging to *Chaetomium*.
Figure 8:
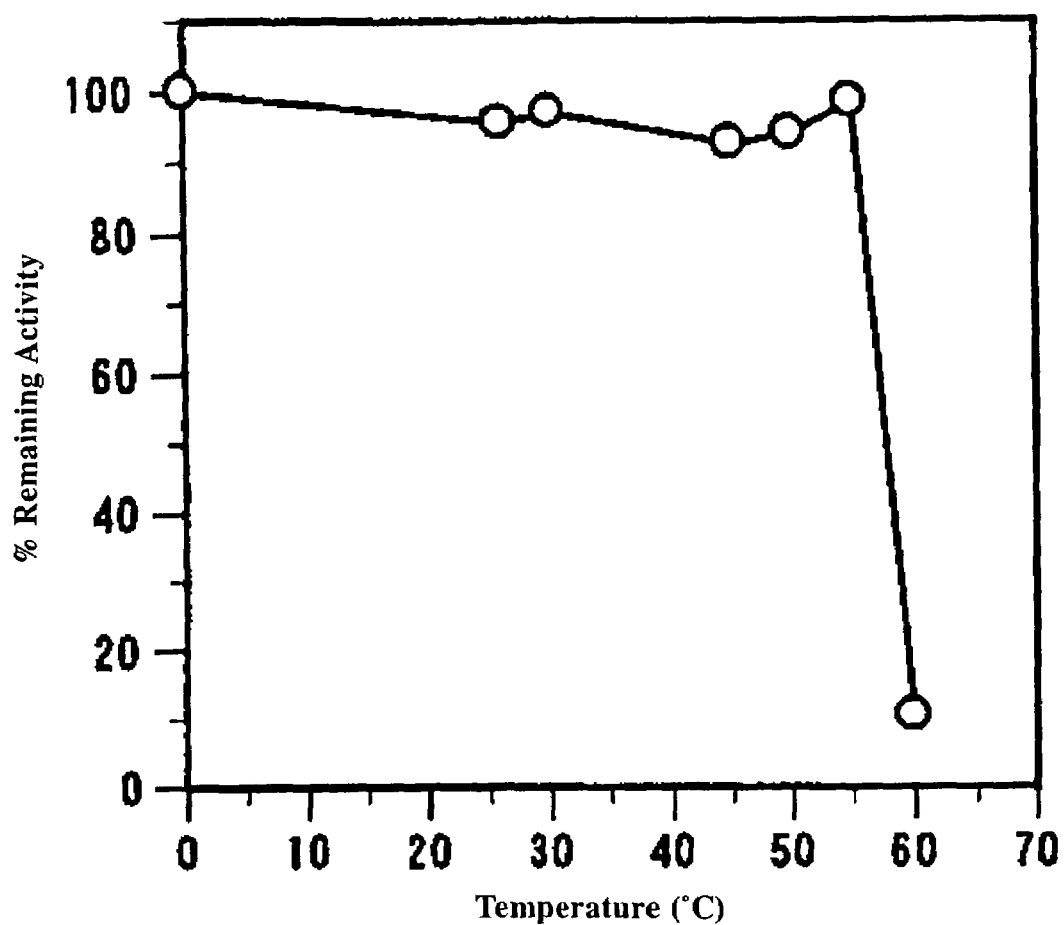
FIG. 8 shows the thermostability of the inventive oxidase produced by a filamentous fungus belonging to *Chaetomium*.

From these results, the optimum temperature range of the inventive oxidase was determined to be from 20 to 45° C.
(d) Thermostability The inventive oxidase was treated with 200 mM potassium phosphate buffer (pH 8.0) at different temperatures for 10 minutes and the thermostability thereof was determined. The results are shown in FIG. 8 which illustrates that the inventive oxidase remained stable up to about 55° C.
(e) Stable pH range The inventive oxidase was treated with 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. for 10 minutes, and the remaining activity thereof was determined. The results are shown in FIG. 6. The inventive oxidase exhibited its maximum activity at around pH 7.0 and remaining activities of 70% or higher at pH 5.0–9.0.

From these results, the stable pH range for the inventive oxidase was determined to be pH 5.0–9.0.

Example 7

Figure 9:
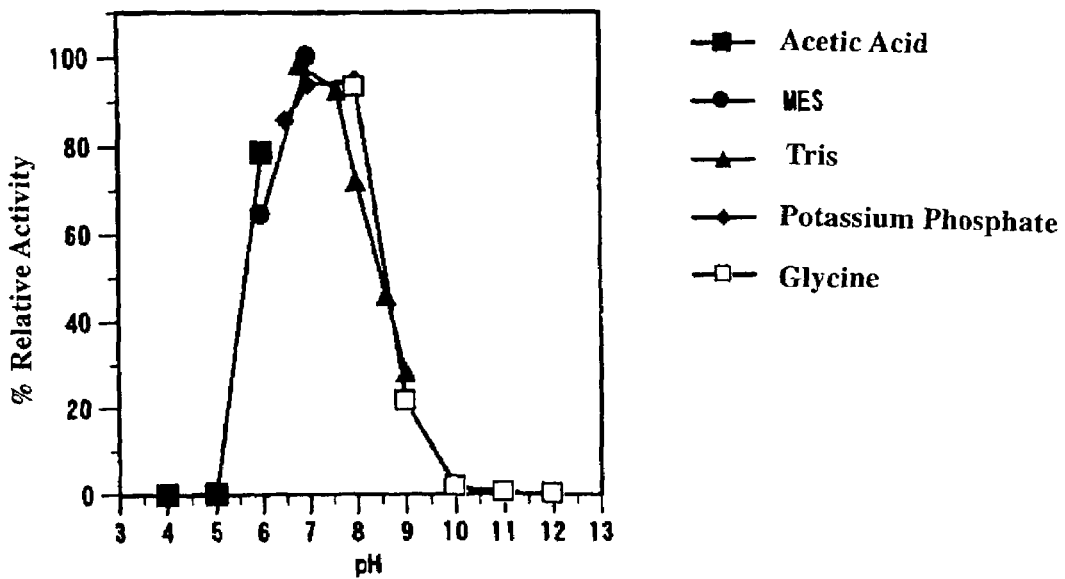
FIG. 9 shows the optimum pH for the inventive oxidase produced by a filamentous fungus belonging to *Coniochaeta* which has less action on ε-fructosyl lysine.

The Physiochemical Properties of the Inventive Oxidase Produced by *Coniochaeta* sp. Which Has Less Action on ε-fructosyl Lysine The physiochemical properties of the inventive oxidase produced by *Coniochaeta* sp. NISL 9330 (FERM BP-7798) obtained in Example 5 will be described below.
(a) Activity and substrate specificity The activity of the inventive oxidase was assayed by the above-described enzyme activity assay using, as substrate, fructosyl valyl histidine, fructosyl glycine or ε-fructosyl lysine. The inventive oxidase exhibited 61% relative activity for ε-fructosyl lysine and 39% for fructosyl glycine when compared to 100% activity for fructosyl valyl histidine, which shows that the enzyme had less action on ε-fructosyl lysine.
(b) Optimum pH Enzyme reaction was monitored in 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. The results are shown in FIG. 9. The inventive oxidase exhibited its maximum activity at pH 7.0. It still exhibited relative activities of 70% or higher at pH 6.0–8.0 when compared to the maximum activity (100%) obtained at around pH 7.0. From these results, the optimum pH for the inventive oxidase was determined to be pH 6.0–8.0, and most preferably pH 7.0.

(c) Optimum temperature range

Figure 11:
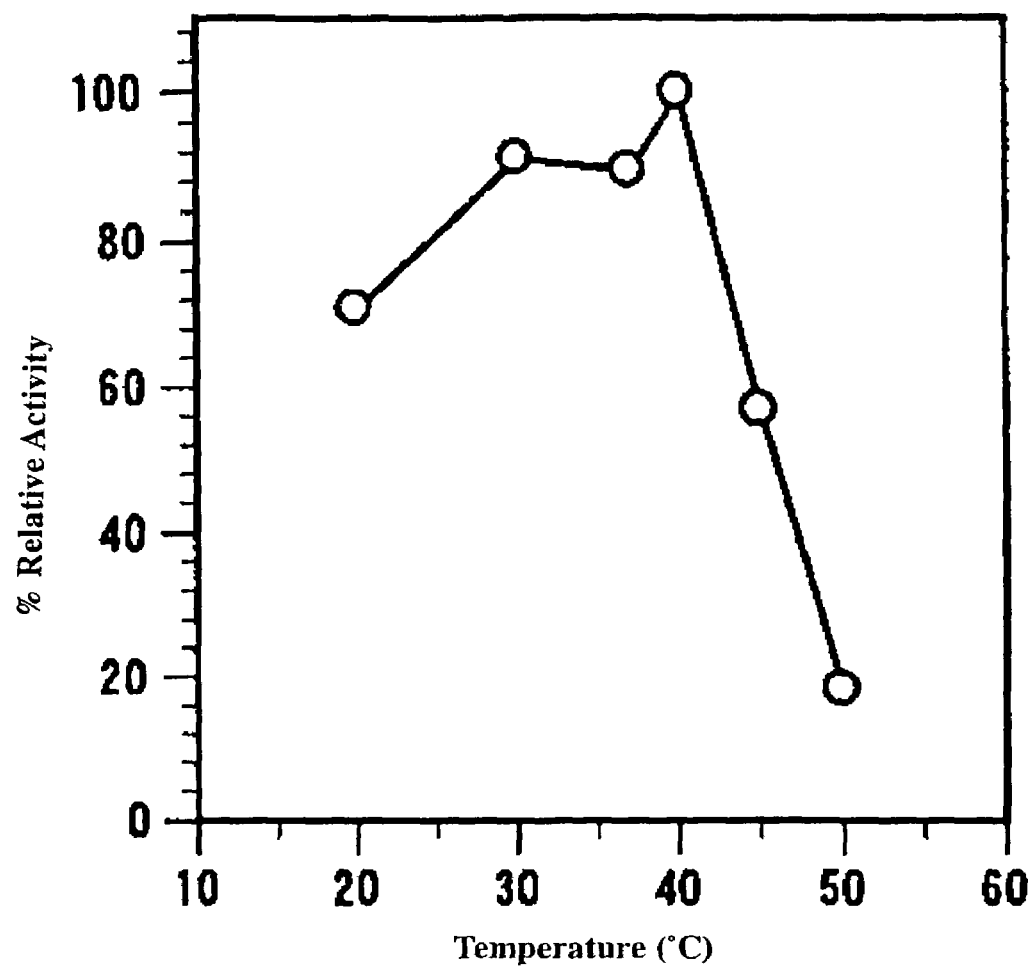
FIG. 11 shows the optimum temperature range for the inventive oxidase produced by a filamentous fungus belonging to *Coniochaeta* which has less action on ε-fructosyl lysine.

The activity of the inventive oxidase was assayed at different temperatures using reaction solutions which consisted of the same compositions as those used in the above-described activity assay. The results are shown in FIG. 11. The enzyme exhibited its maximum activity (100%) at around 40° C. and relative activities of 60% or higher at 20–40° C.

From these results, the optimum temperature range of the inventive oxidase was determined to be from 20 to 40° C.

(d) Thermostability

Figure 12:
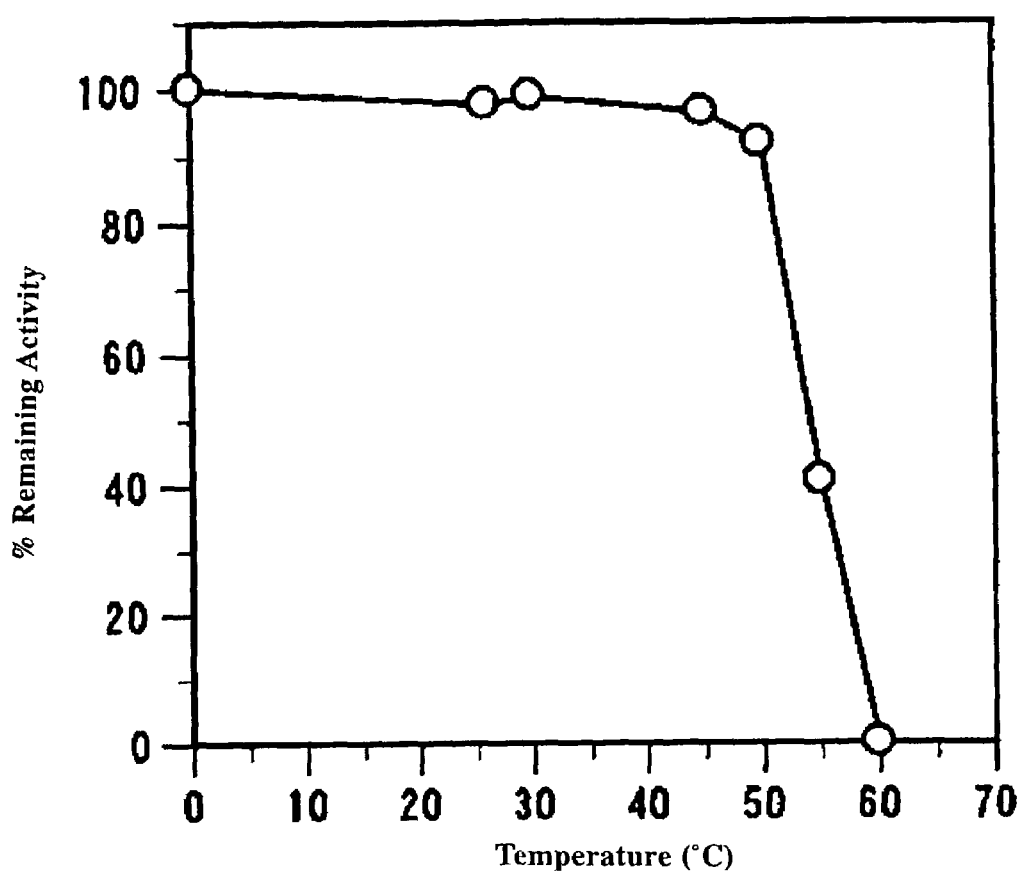
FIG. 12 shows the thermostability of the inventive oxidase produced by a filamentous fungus belonging to *Coniochaeta* which has less action on ε-fructosyl lysine.

The inventive oxidase was treated with 200 mM potassium phosphate buffer (pH 8.0) at different temperatures for 10 minutes and the thermostability thereof was determined. The results are shown in FIG. 12 which illustrates that the inventive oxidase remained stable up to about 50° C.

(e) Stable pH range

Figure 10:
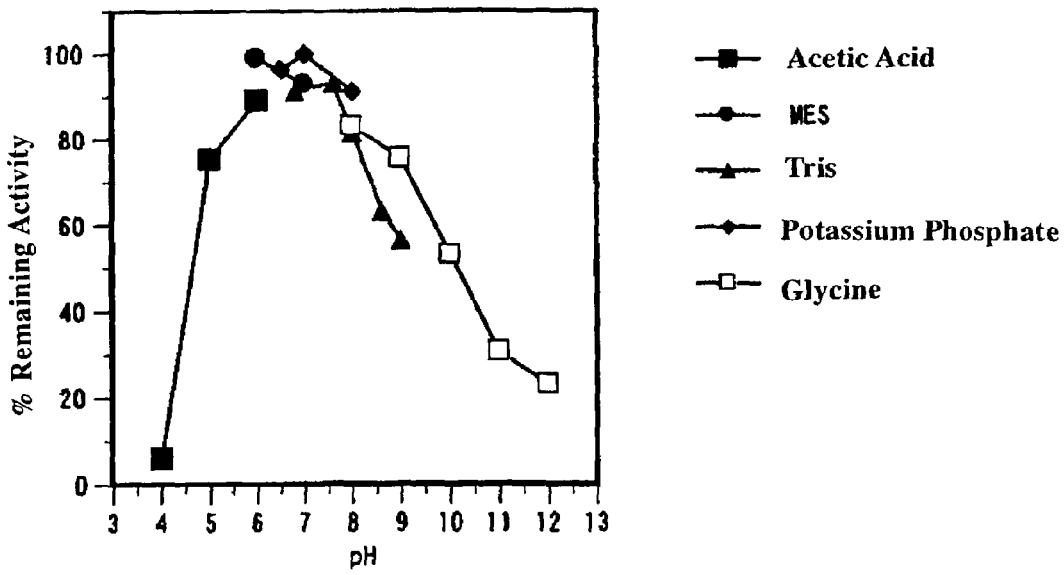
FIG. 10 shows the stable pH range for the inventive oxidase produced by a filamentous fungus belonging to *Coniochaeta* which has less action on ε-fructosyl lysine.

The inventive oxidase was treated with 200 mM acetic acid buffer (pH 3.0–6.0), 200 mM MES-NaOH (pH 6.0–7.0), 200 mM Tris buffer (pH 6.8–9.0), 200 mM potassium phosphate buffer (pH 6.5–8.0) or 200 mM glycine buffer (pH 8.0–12.0) at the indicated pH values at 30° C. for 10 minutes, and the remaining activity thereof was determined. The results are shown in FIG. 10. The inventive oxidase exhibited its maximum remaining activity at around pH 7.0 and remaining activities of 70% or higher at pH 5.0–9.0.

From these results, the stable pH range for the inventive oxidase was determined to be pH 5.0–9.0.

Example 8

Preparing the Inventive Oxidase Produced by *Eupenicillium terrenum* which Has Less Action on ε-fructosyl Lysine

*Eupenicillium terrenum* ATCC 18547 cells were inoculated on 0.05 L of a medium (0.1% yeast extract, 0.1% malt extract, 0.1% potassium dihydrogenphosphate, 0,05% magnesium sulfate, pH 7.3) contained in a 0.15 L Erlenmeyer flask, and grown by rotary shaking culture at 120 rpm, 25° C. for 3 days. Next, the culture (seed) was dispensed (10 mL/flask) into 5 L Erlenmeyer flasks (each containing 1 L of the above-described medium) and grown by rotary shaking culture at 100 rpm, 25° C. for 4 days. Cells were collected from the culture solution by filtration using a Buchner funnel with a filter. The cells obtained were then frozen for storage at −80° C.

Frozen cells (collected from 6 L of culture solution) were suspended in 500 mL of buffer F (10 mM phosphate buffer, 1 mM EDTA, 5% glycerol, 0,5 mM PMSF, pH 8), and disrupted by a French press. The suspension containing disrupted cells was centrifuged at 9,000 rpm for 15 minutes, and buffer F was added to the supernatant to give a crude enzyme solution (500 mL). Ammonium sulfate was then added slowly to the crude enzyme solution to 40% saturation to precipitate an excess amount of protein. The solution was then left to stand at 4° C. overnight and then centrifuged at 9,000 rpm, 4° C. for 15 minutes to collect supernatant.

Further, ammonium sulfate was added slowly to the supernatant to 60% saturation to precipitate protein. The supernatant solution was left to stand at 4° C. overnight, followed by centrifugation (9,000 rpm, 4° C., 15 minutes) to collect precipitant.

The precipitant was dissolved in 10 ml of buffer G (10 mM phosphate buffer, 1 mM EDTA, 5% glycerol, 0.2 M NaCl, pH 8) followed by buffer replacement with PD-10 (available from Amersham Biotech), and then applied to an UltrogelAcA34 (available from IBF Biotechnics) column (2.8 cm×85 cm) pre-equilibrated with buffer G. The column was eluted with 1 L of buffer G to collect active fraction.

The active fraction obtained was concentrated in CentriPrep 10 (available from Amicon) followed by buffer replacement with buffer F, and then applied to a Q Sepharose FF (available from Amersham Biotech) column (1.0 cm×8 cm).

Elution was performed using a linear gradient from buffer H (10 mM phosphate buffer, 1 mM EDTA, 5% glycerol, pH 8) to buffer I (10 mM phosphate buffer, 1 mM EDTA, 5% glycerol, 0.5 M NaCl, pH 8).

The active fraction obtained was again concentrated in CentriPrep 10 (available from Amicon) and then applied to POROS PE (available from Perceptive Biosystems). Elution was performed using a linear gradient from buffer D to buffer E. Protein amount was monitored at O.D. 280 nm using a flow rate of 2ml/min. Active fraction was eluted at about 0.01 M ammonium sulfate. Obtained active fraction was analyzed by SDS-PAGE to confirm a single band (molecular weight=about 53 kDa). The active fraction obtained was used to determine its physiochemical properties as described below.

Example 9

The Physiochemical Properties of the Inventive Oxidase Produced by *Eupenicillium terrenum* which Has Less Action on ε-fructosyl Lysine The physiochemical properties of the inventive oxidase produced by *Eupenicillium terrenum* ATCC 18547 which has less action on ε-fructosyl lysine were as described below.

(a) Activity and substrate specificity

The activity of the inventive oxidase was assayed by the above-described enzyme activity assay using, as substrate, fructosyl valyl histidine, fructosyl glycine or ε-fructosyl lysine. The inventive oxidase with less action on ε-fructosyl lysine exhibited 182% relative activity for fructosyl glycine and 9.78% for ε-fructosyl lysine when compared to 100% activity for fructosyl valyl histidine, indicating that the inventive oxidase had high specificity for fructosyl valyl histidine and fructosyl glycine.

(b) Optimum pH

Figure 13:
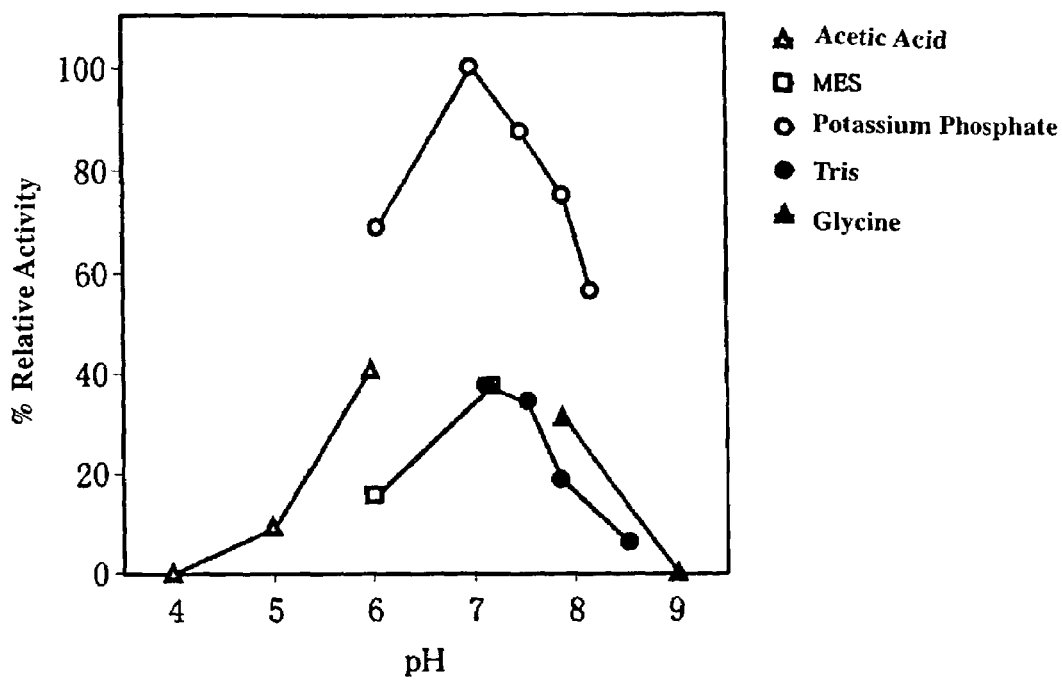
FIG. 13 shows the optimum pH for the inventive oxidase produced by a filamentous fungus belonging to *Eupenicillium* which has less action on ε-fructosyl lysine.

Enzyme reaction was monitored in 200 mM acetic acid buffer (pH 4.0–6.0), 200 mM MES-NaOH (pH 6.0–7.0), 200 mM Tris buffer (pH 7.0–8.5), 200 mM potassium phosphate buffer (pH 6.0–8.0) or 200 mM glycine buffer (pH 8.0–9.0) at the indicated pH values at 30° C. The results are shown in FIG. 13. The inventive oxidase with less action on ε-fructosyl lysine exhibited its maximum activity in potassium phosphate buffer at pH 7.0. It still exhibited relative activities of 70% or higher in the same buffer at pH 6.0–8.0 when compared to the maximum activity (100%) at around pH 7.0. From these results, the optimum pH for the inventive oxidase with less action on ε-fructosyl lysine was determined to be pH 6.0–8.0, and most preferably pH 7.0.

(c) Km value for fructosyl valyl histidine

In the above-described activity assay, activity was monitored using different concentrations of fructosyl valyl histidine (substrate), and Michaelis constant (Km) was determined from a Lineweaver-Burk plot. The Km value of the enzyme for fructosyl valyl histidine was found to be 4.25 mM.

(d) Optimum temperature range

Figure 15:
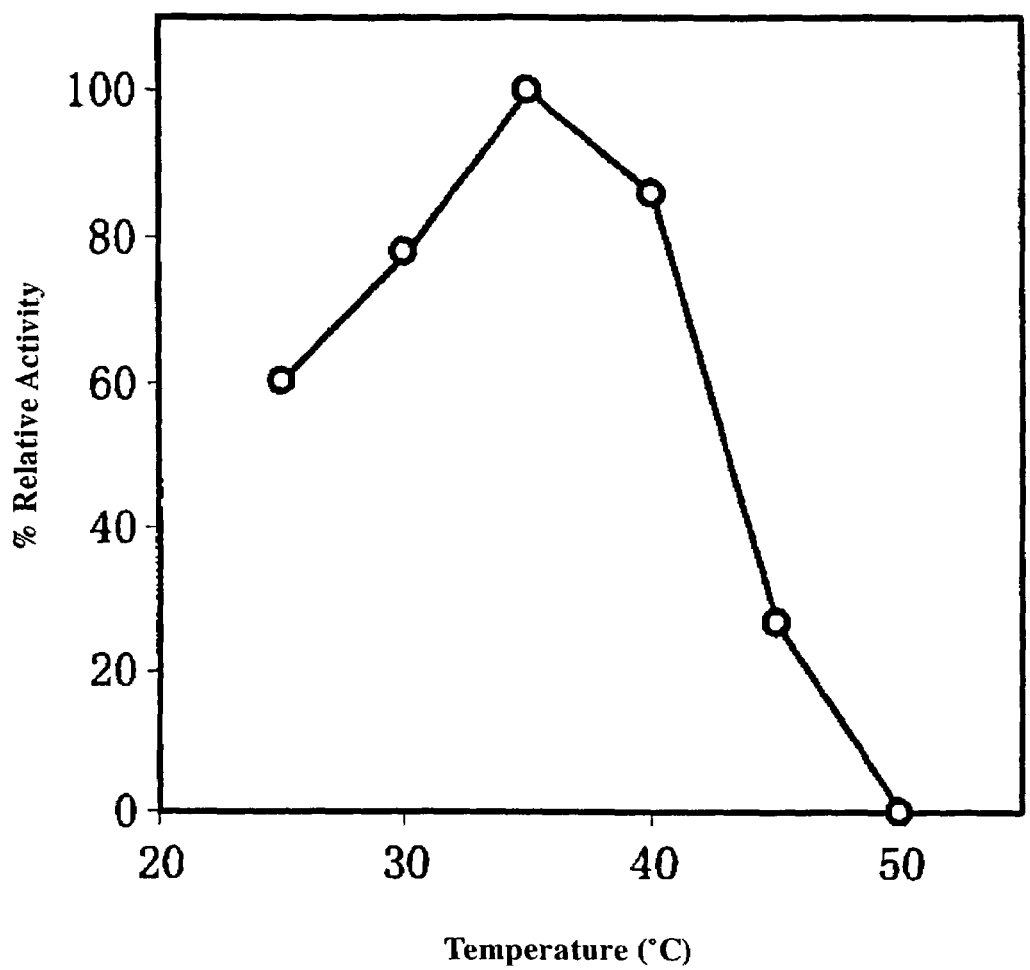
FIG. 15 shows the optimum temperature range for the inventive oxidase produced by a filamentous fungus belonging to *Eupenicillium* which has less action on ε-fructosyl lysine.

The activity of the inventive oxidase was assayed at different temperatures using reaction solutions which consisted of the same compositions as those used in the above-described activity assay. The results are shown in FIG. 15. The enzyme exhibited its maximum activity (100%) at around 35° C. and relative activities of 60% or higher at from 25 to 40° C.

From these results, the optimum temperature range of the inventive oxidase with less action on ε-fructosyl lysine was determined to be 25–40° C.

(e) Thermostability

Figure 16:
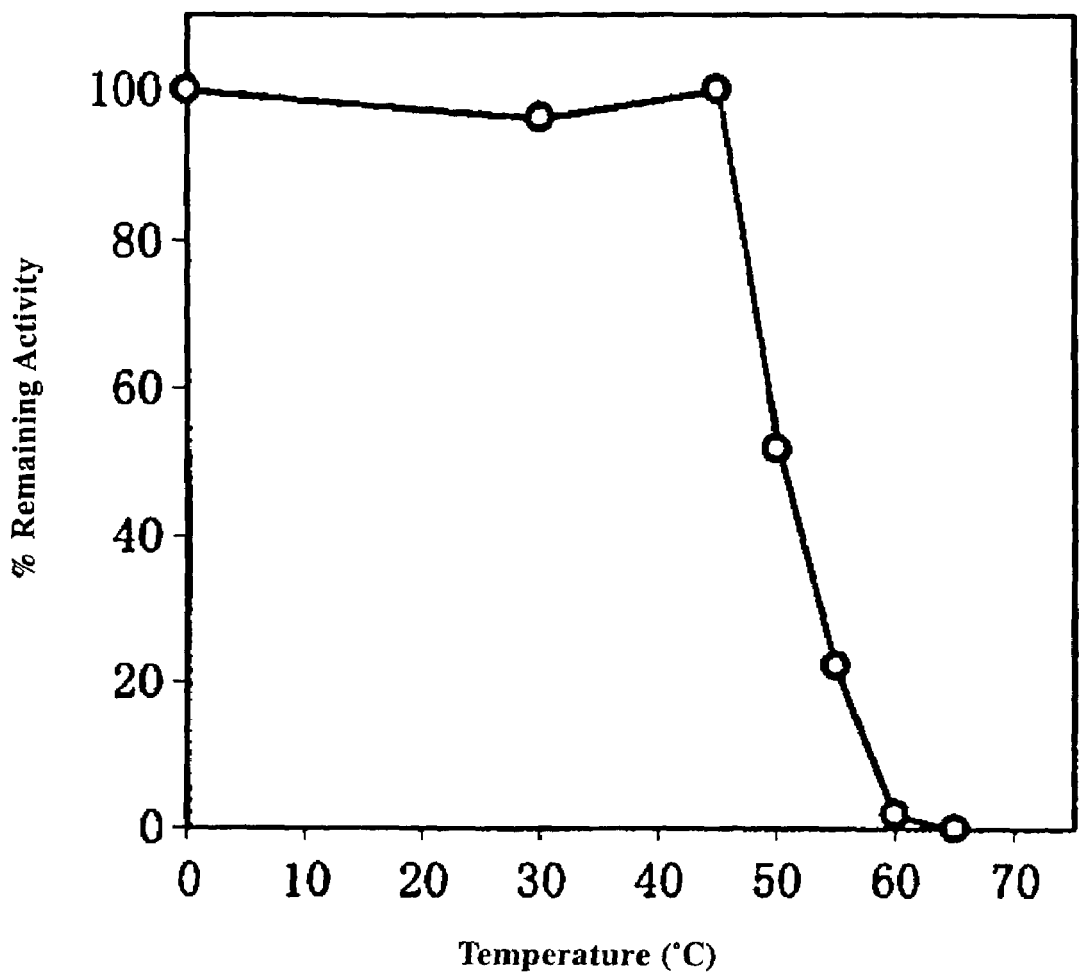
FIG. 16 shows the thermostability of the inventive oxidase produced by a filamentous fungus belonging to *Eupenicillium* which has less action on ε-fructosyl lysine.

The inventive oxidase was treated with 200 mM potassium phosphate buffer (pH 8.0) at different temperatures for 10 minutes and the remaining activity thereof was monitored. The results are shown in FIG. 16 which illustrates that the inventive oxidase with less action on ε-fructosyl lysine exhibited high stability, with approximately 100% remaining activity up to about 45° C.

(f) Stable pH range

Figure 14:
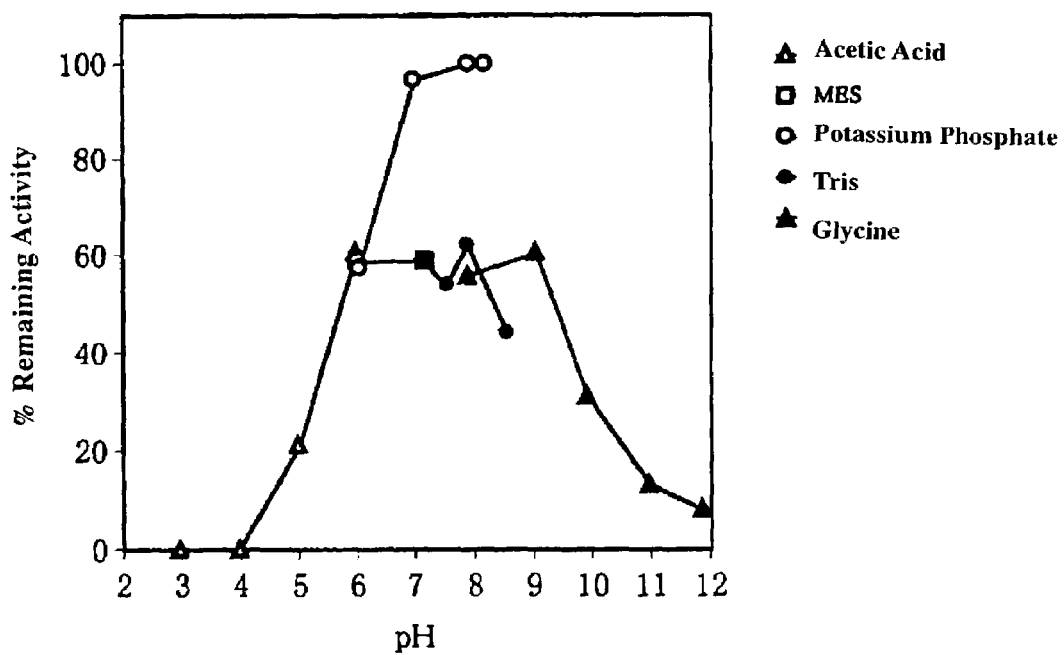
FIG. 14 shows the stable pH range for the inventive oxidase produced by a filamentous fungus belonging to *Eupenicillium* which has less action on ε-fructosyl lysine.

The inventive oxidase was treated with 200 mM acetic acid buffer (pH 3.0–6.0), 200 mM MES-NaOH (pH 6.0–7.0), 200 mM Tris buffer (pH 7.0–8.5), 200 mM potassium phosphate buffer (pH 6.0–8.0) or 200 mM glycine buffer (pH 8.0–12.0) at the indicated pH values at 30° C. for 10 minutes, and the remaining activity thereof was monitored. The results are shown in FIG. 14. The inventive oxidase exhibited its maximum activity in potassium phosphate buffer at pH 8.0 and remaining activities of 60% or higher at pH 6.0–9.0.

From these results, the stable pH range for the inventive oxidase with less action on ε-fructosyl lysine was determined to be pH 6.0–9.0.

(g) Molecular weight

Molecular weight was determined by SDS-PAGE using Multigel 10/20 (available from DAIICHI PURE CHEMICALS CO., LTD.). The molecular weight of inventive oxidase with less action on ε-fructosyl lysine was about 53,000.

(h) Identifying reaction product

Reaction solution was assayed by HPLC to identify reaction products. First, 50 μl of reaction solution (2 mM fructosyl valyl histidine, 5 mM phosphate buffer (pH 8.0), 0.003U of the inventive oxidase) was incubated at 37° C. for 2 hours, diluted (10×) and then assayed for the reaction products in a TSK gel Amide-80 column (available from Tosoh Co., Ltd.). Similarly, a control sample was obtained by using a buffer instead of the enzyme and assayed. As a result, a peak was detected only for fructosyl valyl histidine in the control sample, while in the enzyme sample a peak was detected only for valyl histidine with no peak detected for fructosyl valyl histidine. From these results, it was confirmed that the inventive oxidase catalyzes the decomposition of fructosyl valyl histidine to produce valyl histidine. Further, it was suggested that this reaction cleaved an α-ketoamine bond, as in the glycated amino acid oxidase reaction.

Example 10

The Inventive Oxidases Produced by Filamentous Fungi Belonging to the Genus *Eupenicillium* which Have Less Action on ε-fructosyl Lysine Among the inventive filamentous fungi selected in Experimental Example 1, in addition to *Eupenicillium terrenum* ATCC 18547, three strains of filamentous fungi belonging to the genus *Eupenicillium* were obtained which produce the inventive oxidases with less action on ε-fructosyl lysine. These filamentous fungi belonging to the genus *Eupenicillium* (i.e., *Eupenicillium terrenum* ATCC 18547, *Eupenicillium senticosum* IFO 9158, *Eupenicillium idahoense* IFO 9510, and *Eupenicillium euglaucum* IFO 31729) were used to prepare the inventive oxidases with less action on ε-fructosyl lysine. The physiochemical properties of the oxidases obtained were then assayed. The results are shown in Table 3.

Each of the above-described 4 strains was cultured on the above-described enzyme induction media 1 (3 ml) at 30° C. for 4 days and then cells were collected. The cells obtained were suspended in 0.9 ml of a lysis buffer, disrupted by using a Physcotron and by ultrasonication, added with Triton X-100 to a final concentration of 0.5%, and centrifuged at 15,000 rpm, 4° C. for 10 minutes to collect supernatant (crude enzyme sample). Each of the crude enzyme samples obtained was assayed for its activity for fructosyl valyl histidine (FVH), fructosyl glycine (FG) or ε-fructosyl lysine (εFL). The activities were indicated as % relative activities when compared to the activity for fructosyl valyl histidine (100%). Moreover, each crude enzyme sample was heat-treated at 45° C. for 10 minutes and its activity for fructosyl valyl histidine was assayed. The results were compared to the activity obtained before heat-treatment. As shown in Table 3, all the strain samples tested acted on fructosyl valyl histidine and fructosyl glycine, although the level of activity per medium was different depending on the strains. Particularly, two out of the four stains exhibited 2-fold or higher activities, one exhibited 3-fold or higher activity, and the remaining one exhibited even 10-fold or higher activity for fructosyl valyl histidine when compared to their activities for ε-fructosyl lysine. Under the above-described heat-treatment conditions, all of the inventive oxidase samples obtained from the 4 strains exhibited remaining activities of 90% or higher, indicating that they are very stable.

TABLE 3

| Strain | Activity per medium (U/L) | Substrate specificity (% relative activity) | | | Thermo-stability (%) |
| --- | --- | --- | --- | --- | --- |
| | | FVH | FG | εFL | |
| *Eupenicillium terrenum* ATCC 18547 | 2.8 | 100 | 182 | 9.78 | 100 |
| *Eupenicillium senticosum* IFO 9158 | 0.52 | 100 | 83.1 | 30.8 | 92.9 |
| *Eupenicillium idahoense* IFO 9510 | 0.25 | 100 | 86.1 | 41.0 | 90.0 |
| *Eupenicillium euglaucum* IFO 31729 | 0.095 | 100 | 83.3 | 38.9 | 116 |

Example 11

Reaction of the Inventive Oxidase with Products Obtained by Treatment of Glycated Peptide with Protease Glycated hemoglobin (HbA$_{1c}$) may be treated with endoproteinase Glu-C to liberate α-glycated hexapeptide (fructosyl Val-His-Leu-Thr-Pro-Glu) from the glycated hemoglobin β-chain (Clin. Chem., 43; 10 1944–1951, 1997). Fructosyl Val-His-Leu-Thr-Pro-Glu (available from PEPTIDE INSTITUTE, INC), which is the same substance as the α-glycated hexapeptide, was used in the following experiment.

(1) Preparation of reagents (A) 20 mM α-glycated hexapeptide

α-glycated hexapeptide (fructosyl Val-His-Leu-Thr-Pro-Glu, MW=856, available from PEPTIDE INSTITUTE, INC) (3.434 mg) was dissolved in 0.2 ml of water.

(B) Protease

Molsin (15 mg, available from Kikkoman Corp.) was dissolved in 0.2 ml of buffer (10 mM acetate buffer, pH 3.0)

(C) 0.2 M acetate buffer, pH 3.0

(D) Reaction substrate (a) Products obtained by digesting α-glycated hexapeptide with protease A (100 μl), B (5 μl) and C (5 μl) were mixed in a microtube and incubated at 37° C. for 17 hours. The reaction solution was then filtered using Microcon 10 (available from Amicon) to remove protease.

(b) 20 mM fructosyl glycine (control)

Fructosyl glycine (4.5 mg) was dissolved in 1 ml of water.

(E) Developer solution

Developer solution consisted of the following materials:

5 μl of 10 mg/ml 4-aminoantipyrine;

7.5 μl of 2% 2,4-dichlorophenol sulfate;

1 μl of 3300 U/ml peroxidase;

100 μl of 1M phosphate buffer (pH 8); and 286.5 μl of water.

(F) The inventive oxidases (a) Enzyme purified from *Achaetomiella virescens* ATCC 32393

(b) Enzyme purified from *Eupenicillium terrenum* ATCC 18547

(c) Enzyme purified from *Coniochaeta* sp. NISL 9330 (FERM BP-7798)

(d) 20 mM phosphate buffer, pH 8.0

(2) Reaction assay

Reaction substrate (D: a, b) (20 μl), developer solution (E) (20 μl) and the inventive oxidase (F: a–d) (10 μl) were mixed in 96-well assay plates for reaction. Each plate was monitored at 510 nm using a plate reader (Immuno Mini NJ-2300, available from Nalge Nunc International K. K.) for 70 minutes. The results are shown as % relative activity when compared to 100% activity for fructosyl glycine (Table 4). N. D. indicates that color development was undetectable. It was confirmed that all of the inventive oxidases were reactive with the protease-digested products of α-glycated hexapeptide.

TABLE 4

|  | *Achaetomiella virescens* ATCC 32393 | *Eupenicillium terrenum* ATCC 18547 | *Coniochaeta* sp. NISL 9330 | Phosphate buffer |
|---|---|---|---|---|
| α-glycated hexapeptide | 9.2% | 9.5% | 10.0% | N.D. |
| fructosyl glycine | 100% | 100% | 100% | N.D. |

Example 12

Cloning and Expression of the Inventive Gene (Derived from *Coniochaeta* sp.) by Using Transformant (1) Preparation of *Coniochaeta* sp. mRNA

*Coniochaeta* sp. was inoculated on 0.05 L of a medium (0.4% yeast extract, 1% malt extract, 2% glucose, 0.1% tryptone, 0.1% potassium dihydrogenphosphate, 0.05% magnesium sulfate, pH 7) contained in a 0.15 L Erlenmeyer flask, and grown by rotary shaking culture at 120 rpm, 30° C. for 1 day. Next, the culture (seed) was dispensed (1 ml/flask) into 1L Erlenmeyer flasks (each containing 0.5 L of the above-described medium) and grown by rotary shaking culture at 120 rpm, 30° C. for 2 days. The culture solution was centrifuged at 12,000 rpm for 10 minutes to collect cells. The cells obtained were disrupted in a mortar with a pestle in the presence of liquid nitrogen, suspended in 10 ml of RNA extraction reagent ISOGEN (available from Wako Pure Chemical Industries, Ltd.), and centrifuged at 2,700 rpm for 5 minutes to obtain RNA fraction, from which mRNA (0.51 mg) was obtained according to the method described in Current Protocols in Molecular Biology (WILEY, Interscience, 1989).

(2) Synthesis of primers

Fructosyl peptide oxidase (about 10 μg) purified according to the method described in Example 5 was digested with trypsin and subjected to preparative HPLC to obtain 7 peptides. The 7 peptides obtained were read on an ABI 470A protein sequencer (available from Perkin-Elmer Corp.) to determine the internal amino acid sequences. The sequences determined were used to synthesize primers shown in SEQ ID NOS: 5 and 6 utilizing Amersham Biotech Custom Synthesis Service.

(3) RT-PCR

A first reaction solution was prepared using the following materials:

| | |
|---|---|
| Mg Cl$_2$ | 5 mM; |
| *10x RNA PCR buffer | 2 μl; |
| H$_2$O | 8.5 μl; |
| dNTPs | 1 mM each; |
| RNase inhibitor | 1 U/μl; |
| *AMV reverse transcriptase XL | 0.25 U/μl; |
| *oligo dT adapter primer | 0.125 μM; and |
| mRNA | 1 μg. |

Note)
*: available from Takara Bio Inc.

The first reaction solution was left to stand at 42° C. for 30 minutes for reverse transcription reaction, denatured at 99° C. for 5 minutes and then stored at 5° C.

Next, a second reaction solution was prepared using the following materials:

| | |
|---|---|
| Primer (SEQ ID NO: 5) | 0.2 µM; |
| Primer (SEQ ID NO: 6) | 0.2 µM; |
| *10x RNA PCR buffer | 8 µl; |
| Magnesium chloride | 2.5 mM; |
| *Taq polymerase | 2.5 U; and |
| H₂O | (to a final total volume of 80 µl). |

Note)
*: available from Takara Bio Inc.

Then, 80 µl of the second reaction solution was added to the tube containing reverse-transcription, and 30 cycles of PCR amplification were performed. The amplification cycle consisted of denaturing at 94° C. for 30 seconds, annealing at 62° C. for 30 seconds and extension at 72° C. for 1.5 minutes.

After completion of PCR reaction, the reaction solution was subjected to electrophoresis on agarose gel to confirm a band at approximately 0.77 kb, which seemed to be the fragment of interest. The region of the gel containing the band was excised and DNA fragment was purified in GENECLEAN II (available from BIO 101 Inc.

(4) Analysis of purified DNA fragment

Purified DNA fragment was sequenced and analyzed using a 370A DNA sequencing system (available from Perkin-Elmer Corp.) to confirm the presence of the above-described amino acid sequence (Leu-Ser-Lys-Met-Pro-Leu-Leu-Gln-Arg) in the putative amino acid sequence deduced from the nucleotide sequence determined. From these results, it was confirmed that the DNA fragment obtained by the above-described RT-PCR amplification contained a portion of the genetic sequence encoding the fructosyl peptide oxidase derived from *Coniochaeta* sp.

(5) Analysis of the downstream region by 3'-RACE

First, a primer (SEQ ID NO: 7) was designed using the DNA sequence data obtained as described above and synthesized utilizing Amersham Biotech Custom Synthesis Service. This primer, the above-described mRNA and 3'-Full RACE Core Set (available from Takara Bio Inc.) were used to perform RT-PCR to amplify the 3'-unknown region. The reaction solution was subjected to electrophoresis on agarose gel followed by purification and extraction of an about 500 bp DNA fragment using Reco Chip (available from Takara Bio Inc.). The DNA fragment purified was then sequenced and analyzed in a DNA sequencer to confirm the presence of the same sequence as the 3' sequence of a portion of the genetic sequence encoding the fructosyl peptide oxidase derived from *Coniochaeta* sp. in the 5'-region of the nucleotide sequence determined. Further, the presence of the above-described amino acid sequence (Phe-Gln-Asp-Lys-Glu-Leu-Phe-Asn-Arg) was confirmed in the putative amino acid sequence deduced from the nucleotide sequence determined.

(6) Analysis of the upstream region by 5'-RACE

First, primers (SEQ ID NOS: 8–12) were designed using the DNA sequence data obtained as described above and synthesized utilizing Amersham Biotech Custom Synthesis Service. These primers, the above-described mRNA and 5'-Full RACE Core Set (available from Takara Bio Inc.) were used to perform RT-PCR to amplify the 5'-unknown region. The reaction solution was subjected to electrophoresis on agarose gel followed by purification and extraction of an about 450 bp DNA fragment using Reco Chip (available from Takara Bio Inc.). The DNA fragment purified was then sequenced and analyzed in a DNA sequencer to confirm the presence of the same sequence as the 540 sequence of a portion of the genetic sequence encoding the fructosyl peptide oxidase derived from *Coniochaeta* sp. in the 3'-region of the nucleotide sequence determined. Further, the presence of the above-described amino acid sequence (Ser-Gly-Tyr-Ala-Pro-Ala-Asn-Ile-Thr) was confirmed in the putative amino acid sequence deduced from the nucleotide sequence determined.

(7) Obtaining genetic fragments by RT-PCR

Translation start and stop codons were deduced from the above-described 3 nucleotide sequences, and primer DNAs (SEQ ID NOS: 13 and 14) for the N- and C-terminal regions were synthesized utilizing Amersham Biotech Custom Synthesis Service. These primers and the above-described mRNA were used to perform RT-PCR. The reaction solution was subjected to electrophoresis on agarose gel to confirm the presence of an approximately 1.3 kb band. Then, DNA fragment contained in the band was purified and extracted using Reco Chip (available from Takara Bio Inc.). Further, plasmid pKK223-3 (available from Amersham) was digested with restriction enzyme EcoRI, blunt-ended using BluntingKit (available from Takara Bio Inc.) and ligated with the DNA fragment purified and extracted as described above. The ligated DNA was then used to transform *E. coli* JM 109. The plasmid pKK223-3-CFP obtained as described above was deposited at the International Patent Organism Depositary, the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan as FERM BP-8132.

(8) Confirmation of activity

*E. coli* JM 109 (pKK223-3-CFP) cells were grown in 10 ml of TY-medium containing 50 1 µg/ml ampicillin (1% bactotryptone, 0.5% bactoyeast extract, 0.5% NaCl, pH 7.0) by shake-culture at 32° C. to Klett 100 , added with IPTG to a final concentration of 1 mM, and cultured for an additional 3 hours. The culture solution was treated in an Ultrasonic-generator (available from Nissei) for 20 sec.x4 times while cooling on ice. The culture solution was loaded in a micro tube, and centrifuged in a microcentrifuge at 12,000 rpm for 10 minutes to give supernatant and precipitate fractions. The supernatant fraction obtained was transferred to another micro tube, and fructosyl peptide oxidase activity was determined according to the above-described enzyme activity assay to find that JM109 (pKK 223-3-CFP) had 4.74 U/ml fructosyl peptide oxidase activity.

(9) Analysis of gene encoding fructosyl peptide oxidase

Since it was confirmed that *E. coli* JM109 (pKK223-3-CFP) had fructosyl peptide oxidase activity, it became clear that the insert fragment incorporated in pKK223-3-CFP contained the gene encoding fructosyl peptide oxidase. Therefore, the nucleotide sequence of the plasmid DNA was determined using a 370A DNA sequencing system (available from Perkin-Elmer Corp.). The nucleotide sequence of the plasmid DNA determined and the putative amino acid sequence of the polypeptide which may be translated therefrom are shown in SEQ ID NOS: 2 and 1, respectively. The gene encoding fructosyl peptide oxidase had a 1314 bp coding region which encoded 437 amino acids.

Example 13

Cloning and Expression of the Inventive Gene (Derived from *Eupenicillium terrenum*) by Transformant (1) Preparation of *Eupenicillium terrenum* mRNA

*Eupenicillium terrenum* ATCC 18547 was inoculated on 0.05 L of a medium (0.1% yeast extract, 0.1% malt extract, 0.1% potassium dihydrogenphosphate, 0.05% magnesium sulfate, pH 7.3) contained in a 0.15 L Erlenmeyer flask, and grown by rotary shaking culture at 120 rpm, 25° C. for 3 days. Next, the culture (seed) was dispensed (1 ml/flask) into 1 L Erlenmeyer flasks (each containing 0.5 L of the above-described medium) and grown by rotary shaking culture at 120 rpm, 25° C. for 4 days. The culture solution was centrifuged at 12,000 rpm for 10 minutes to collect cells. The cells obtained were disrupted in a mortar with a pestle in the presence of liquid nitrogen, suspended in 10 ml of RNA extraction reagent ISOGEN (available from Wako Pure Chemical Industries, Ltd.), and centrifuged at 2,700 rpm for 5 minutes to give RNA fraction, from which mRNA was obtained according to the method described in Current Protocols in Molecular Biology (WILEY, Interscience, 1989).

(2) Synthesis of primers

Fructosyl peptide oxidase (about 10 μg) purified according to the method described in Example 8 was digested with trypsin and subjected to preparative HPLC to obtain 6 peptides. The 6 peptides obtained were read on an ABI 470A protein sequencer (available from Perkin-Elmer Corp.) to determine the internal amino acid sequences (Thr-Asn-Val-Trp-Leu-Glu-Ser-Glu, Asp-Leu-Ala-Glu-Met-Pro-Gly, Asn-Phe-Ile-Leu-Ala, Leu-Pro-Asn-Ile-Gly, x-Pro-Thr-Asp-x-Tyr-Pro, Leu-His-Gln-Pro-Tyr-Gly-Ala-x-x-Pro). The sequences determined were used to synthesize primers shown in SEQ ID NOS: 15 and 16 utilizing Amersham Biotech Custom Synthesis Service.

(3) RT-PCR

A first reaction solution was prepared using the following materials:

| | |
|---|---|
| Mg Cl$_2$ | 5 mM; |
| *10x RNA PCR buffer | 2 μl; |
| H$_2$O | 8.5 μl; |
| dNTPs | 1 mM each; |
| RNase inhibitor | 1 U/μl; |
| *AMV reverse transcriptase XL | 0.25 U/μl; |
| *oligo dT adapter primer | 0.125 μM; and |
| mRNA | 1 μg. |

Note)
*: available from Takara Bio Inc.

The first reaction solution was left to stand at 42° C. for 30 minutes for reverse transcription reaction, denatured at 99° C. for 5 minutes and then stored at 5° C.

Next, a second reaction solution was prepared using the following materials:

| | |
|---|---|
| Primer (SEQ ID NO: 15) | 0.2 μM; |
| Primer (SEQ ID NO: 16) | 0.2 μM; |
| *10x RNA PCR buffer | 8 μl; |
| Magnesium chloride | 2.5 mM; |
| *Taq polymerase | 2.5 U; and |
| H$_2$O | (to a final total volume of 80 μl). |

Note)
*: available from Takara Bio Inc.

Then, 80 μl of the second reaction solution was added to the tube containing reverse-transcription, and 30 cycles of PCR amplification were performed. The amplification cycle consisted of denaturing at 94° C. for 30 seconds, annealing at 62° C. for 30 seconds and extension at 72° C. for 1.5 minutes.

After completion of PCR reaction, the reaction solution was subjected to electrophoresis on agarose gel to confirm a band at approximately 0.9 kb, which seemed to be the fragment of interest. The region of the gel containing the band was excised and DNA fragment was purified in GENECLEAN II (available from BIO 101, Inc.)

(4) Analysis of purified DNA fragment

Purified DNA fragment was sequenced and analyzed on a 370A DNA sequencing system (available from Perkin-Elmer Corp.) to confirm the presence of the above-described amino acid sequences (Asn-Phe-Ile-Leu-Ala, Leu-Pro-Asn-Ile-Gly, x-Pro-Thr-Asp-x-Tyr-Pro, Leu-His-Gln-Pro-Tyr-Gly-Ala-x-x-Pro) in the putative amino acid sequence deduced from the nucleotide sequence determined. From these results, it was confirmed that the DNA fragment obtained by the above-described RT-PCR amplification contained a portion of the genetic sequence encoding the fructosyl peptide oxidase derived from *Eupenicillium terrenum*.

(5) Analysis of the downstream region by 3'-RACE

First, a primer (SEQ ID NO: 17) was designed using the DNA sequence data obtained as described above and synthesized utilizing Amersham Biotech Custom Synthesis Service. This primer, the above-described mRNA and 3'-Full RACE Core Set (available from Takara Bio Inc.) were used to perform RT-PCR to amplify the 3'-unknown region. The reaction solution was subjected to electrophoresis on agarose gel followed by purification and extraction of an about 400 bp DNA fragment using Reco Chip (available from Takara Bio Inc.). The DNA fragment purified was then sequenced and analyzed in a DNA sequencer to confirm the presence of the same sequence as the 3' sequence of a portion of the genetic sequence encoding the fructosyl peptide oxidase derived from *Eupenicillium terrenum* in the 5'-region of the nucleotide sequence determined.

(6) Analysis of the upstream region by 5'-RACE

First, primers (SEQ ID NOS: 18–22) were designed using the DNA sequence data obtained as described above and synthesized utilizing Amersham Biotech Custom Synthesis Service. These primers, the above-described mRNA and 5'-Full RACE Core Set (available from Takara Bio Inc.) were used to perform RT-PCR to amplify the 5'-unknown region. The reaction solution was subjected to electrophoresis on agarose gel followed by purification and extraction of an about 600 bp DNA fragment using Reco Chip (available from Takara Bio Inc.). The DNA fragment purified was then sequenced and analyzed in a DNA sequencer to confirm the presence of the same sequence as the 5' sequence of a portion of the genetic sequence encoding the fructosyl peptide oxidase derived from *Eupenicillium terrenum* in the 3'-region of the nucleotide sequence determined.

(7) Obtaining genetic fragments by RT-PCR

Translation start and stop codons were deduced from the above-described 3 nucleotide sequences, and primer DNAs (SEQ ID NOS: 23 and 24) for the N- and C-terminal regions were synthesized utilizing Amersham Biotech Custom Synthesis Service. These primers and the above-described mRNA were used to perform RT-PCR. The reaction solution was then subjected to electrophoresis on agarose gel to confirm the presence of an approximately 1.3 kb band. Then, DNA fragment contained in the band was purified and extracted using Reco Chip (available from Takara Bio Inc.). Further, plasmid pUC19 (available from Takara Bio Inc) was digested with restriction enzyme SmaI, and ligated with the DNA fragment purified and extracted as described above. The ligated DNA was then used to transform E. coli JM 109. The obtained plasmid puc-EFP was deposited at the International Patent Organism Depositary, the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan as FERM BP-8131.

(8) Confirmation of activity

E. coli JM 109 (puc-EFP) cells were grown in 10 ml of TY-medium containing 50 µg/ml ampicillin (1% bactotryptone, 0.5% bactoyeast extract, 0.5% NaCl, pH 7.0) by shake-culture at 30° C. to Klett 100, added with IPTG to a final concentration of 1 mM, and cultured for an additional 3 hours. The culture solution was treated in an Ultrasonic-generator (available from Nissei) for 20 sec.×4 times while cooling on ice. The culture solution was loaded in a microtube, and centrifuged in a microcentrifuge at 12,000 rpm for 10 minutes to obtain supernatant and precipitate fractions. The supernatant fraction obtained was transferred to another microtube and determined for fructosyl peptide oxidase activity according to the above-described enzyme activity assay to find that JM109 (puc-EFP) had a fructosyl peptide oxidase activity of 0.01 U/ml.

(9) Analysis of gene encoding fructosyl peptide oxidase

Since it was confirmed that E. coli JM109 (puc-EFP) had fructosyl peptide oxidase activity, it became clear that the insert fragment incorporated in puc-EFP contained the gene encoding fructosyl peptide oxidase. Therefore, the nucleotide sequence of the plasmid DNA was determined using a 370A DNA sequencing system (available from Perkin-Elmer Corp.). The nucleotide sequence of the plasmid DNA determined and the putative amino acid sequence of the polypeptide which may be translated from the DNA are shown in SEQ ID NOS: 4 and 3, respectively. The gene encoding fructosyl peptide oxidase had a 1314 bp coding region which coded for 437 amino acids.

According to the present invention, novel fructosyl peptide oxidases with a variety of physicochemical properties and a method for producing them are provided. The inventive fructosyl peptide oxidases are advantageous in that they can be used easily as diagnostic enzymes in an assay kit and that they can be mass-produced at low cost, and are therefore useful in the industry. Further, the present invention also provides oxidases which have less action on fructosyl lysine. Those oxidases have improved stability and are particularly useful as enzymes for diagnosing diabetes. The present invention also provides a method for producing those oxidases. In this way, the present invention allows for the development of a kit for clinical diagnosis with improved storage stability. Those oxidases with less action on fructosyl lysine are more useful in the industry.

This application includes part or all of the contents as disclosed in the specification and/or drawings of Japanese Patent Application Nos. 2001-266665, 2001-378151 and 2002-228727, which are priority documents of the present application. All publications, patents and patent applications cited herein are incorporated in the present specification by reference in their entirety.

What is claimed is:

1. An isolated polypeptide:
having fructosyl peptide oxidase activity, which acts on fructosyl valyl histidine in the presence of oxygen to catalyze a reaction that produces α-ketoaldehyde, valyl histidine and hydrogen peroxide,
wherein at least 80% of the activity of said fructosyl peptide oxidase activity remains after a heat treatment at 45° C. for 10 minutes, and
wherein said polypeptide is at least 95% homologous to SEQ ID NO: 3 and has fructosyl peptide oxidase activity.

2. An isolated polypeptide:

having fructosyl peptide oxidase activity, which acts on fructosyl valyl histidine in the presence of oxygen to catalyze a reaction that produces α-ketoaldehyde, valyl histidine and hydrogen peroxide, wherein at least 80% of the activity of said fructosyl peptide oxidase activity remains after a heat treatment at 45° C. for 10 minutes, which comprises SEQ ID NO: 3 or a fragment thereof which has fructosyl peptide oxidase activity.

3. The polypeptide of claim 1 which is active at a temperature ranging from 20–50° C.

4. The polypeptide of claim 1 which is active at a temperature ranging from 25–45° C.

5. The polypeptide of claim 1 which exhibits optimal activity at a pH ranging from 5.0–9.0.

6. The polypeptide of claim 1 which exhibits optimal activity at a pH ranging from 6.0–8.0.

7. The polypeptide of claim 1 which is isolated from a filamentous fungi.

8. The polypeptide of claim 1 which is isolated from *Achaetomiella, Achaetomium, Thielavia, Chaetomium, Gelasinospora, Microascus,* or *Coniochaeta*.

9. The polypeptide of claim 1 which is isolated from *Eupenicillium*.

10. The polypeptide of claim 1, which is isolated from *Eupenicillium senticosum* IFO 9158, *Eupenicillium idahoense* IFO 9510 or *Eupenicillium euglaucum* IFO 31729.

11. An isolated polypeptide:

having fructosyl peptide oxidase activity, which acts on fructosyl valyl histidine in the presence of oxygen to catalyze a reaction that produces α-ketoaldehyde, valyl histidine and hydrogen peroxide, wherein at least 80% of the activity of said fructosyl peptide oxidase activity remains after a heat treatment at 45° C. for 10 minutes, which is isolated from *Eupenicillium terrenum*, wherein said polypeptide is at least 95% homologous to SEQ ID NO: 3 and has fructosyl peptide oxidase activity.

12. The polypeptide of claim 1 which is obtainable from *Eupenicillium terrenum* ATCC 18547.

13. The polypeptide of claim 1 which has a molecular weight of about 52,000 (SDS-PAGE).

14. The polypeptide of claim 1 which has greater activity on fructosyl valyl histidine than on ε-fructosyl lysine.

15. The polypeptide of claim 1 which has no activity on ε-fructosyl lysine.

16. A method for converting fructosyl valyl histidine to valyl histidine comprising:

contacting fructosyl valyl histidine in the presence of oxygen with the polypeptide of claim 1.

17. A method for determining the amount of fructosyl valyl histidine in a sample comprising:

contacting a sample containing fructosyl valyl histidine in the presence of oxygen with the polypeptide of claim 1, and quantifying the amount of fructosyl valyl histidine in said sample by determining the amount of hydrogen peroxide formed compared to the amount of hydrogen peroxide formed by a control sample.

18. A method for determining the amount of a glycated protein in a sample comprising:

digesting a glycated protein, which releases fructosyl valyl histidine when digested, with a protease to produce a sample containing fructosyl valyl histidine, contacting said sample in the presence of oxygen with the polypeptide of claim 1, and quantifying the amount of fructosyl valyl histidine in said sample by determining the amount of hydrogen peroxide formed compared to the amount of hydrogen peroxide formed by a control sample.

* * * * *